United States Patent
Derakhshandeh et al.

(10) Patent No.: US 11,725,147 B2
(45) Date of Patent: Aug. 15, 2023

(54) VOLATILE CONTENT MEASUREMENT IN PROCESS STREAMS SUCH AS FROTH TREATMENT TAILINGS

(71) Applicant: SUNCOR ENERGY INC., Calgary (CA)

(72) Inventors: Babak Derakhshandeh, Calgary (CA); Elco Hollander, Calgary (CA); Cedric Laborde-Boutet, Burnaby (CA); Wayne Brown, Burnaby (CA); William McCaffrey, Burnaby (CA)

(73) Assignee: Suncor Energy Inc.

( * ) Notice: Subject to any disclaimer, the term of this patent is extended or adjusted under 35 U.S.C. 154(b) by 0 days.

(21) Appl. No.: 17/559,940

(22) Filed: Dec. 22, 2021

(65) Prior Publication Data

US 2022/0195304 A1   Jun. 23, 2022

(30) Foreign Application Priority Data

Dec. 22, 2020 (CA) ................ CA 3103502

(51) Int. Cl.
*C10G 1/00* (2006.01)
*G01N 27/64* (2006.01)
*G01N 33/18* (2006.01)

(52) U.S. Cl.
CPC ........... *C10G 1/008* (2013.01); *G01N 27/64* (2013.01); *G01N 33/18* (2013.01)

(58) Field of Classification Search
CPC ........ C10G 1/008; G01N 27/64; G01N 33/18
See application file for complete search history.

(56) References Cited

U.S. PATENT DOCUMENTS

| | | | |
|---|---|---|---|
| 5,127,259 A | 7/1992 | Kahl et al. | |
| 2012/0000830 A1* | 1/2012 | Monaghan | ............ C10G 11/18 208/308 |

FOREIGN PATENT DOCUMENTS

| | | |
|---|---|---|
| CA | 2 768 852 C | 8/2014 |
| CA | 2 911 272 A1 | 5/2016 |

(Continued)

OTHER PUBLICATIONS

Yuan, J., et al., "Volatile organic compounds (VOCs) releasing model from tailingssolvent recovery unit (TSRU) tailings and its sensitivity analysis inenvironment management," Process Safety and Environmental Protection, 141 (2020) 267-277.

(Continued)

*Primary Examiner* — Ellen M McAvoy
*Assistant Examiner* — Chantel L Graham
(74) *Attorney, Agent, or Firm* — Christensen O'Connor Johnson Kindness PLLC

(57) ABSTRACT

Methods, processes and devices are described for measuring a volatile content of a process stream that comprises volatile species, such as light hydrocarbons and/or $H_2S$. The method can include introducing a stripping gas into a sample of the process stream to strip the volatiles therefrom and produce a gas phase comprising vaporized volatiles; detecting the vaporized volatiles in the gas phase to obtain a sample volatile content; and determining the volatile content of the process stream based on the sample volatile content. The method and device can be used to measure a light hydrocarbon content of froth treatment tailings in the context of removing such light hydrocarbons prior to flocculating and dewatering the tailings.

24 Claims, 7 Drawing Sheets

(56) References Cited

FOREIGN PATENT DOCUMENTS

| | | |
|---|---|---|
| CN | 103558334 A | 2/2014 |
| CN | 211477952 U | 9/2020 |
| CN | 211562407 U | 9/2020 |
| CN | 111841262 A | 10/2020 |
| CN | 212236646 U | 12/2020 |
| WO | WO-2011143310 A1 * 11/2011 | ......... B01D 17/0205 |

OTHER PUBLICATIONS

Examination Report dated Nov. 2, 2022, issued in related Canadian Application No. 3143681, filed Dec. 22, 2021, 4 pages.

* cited by examiner

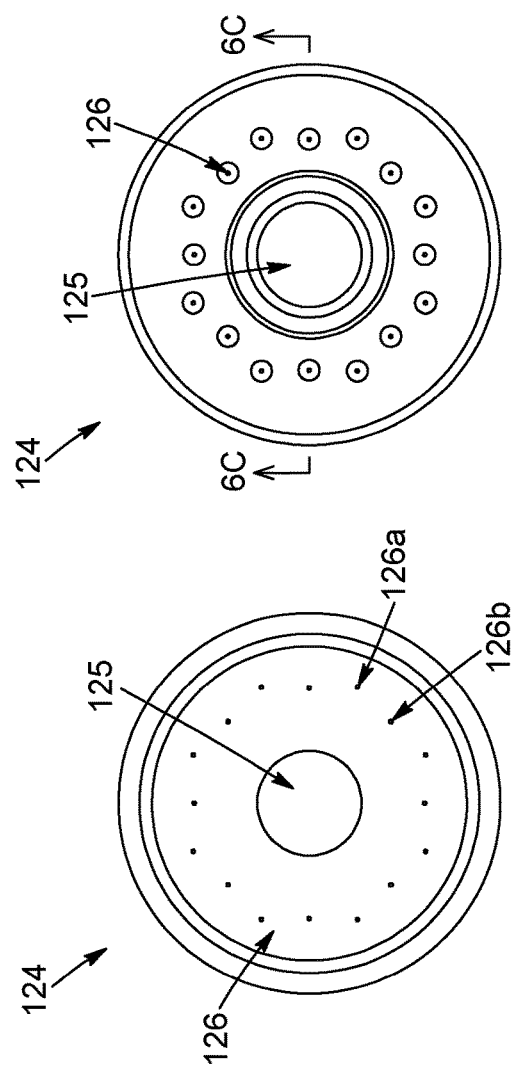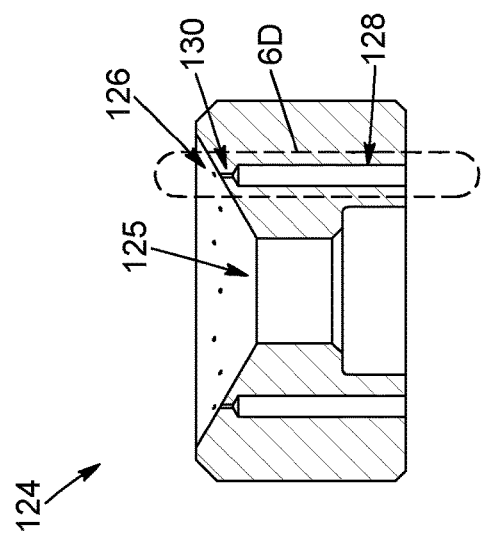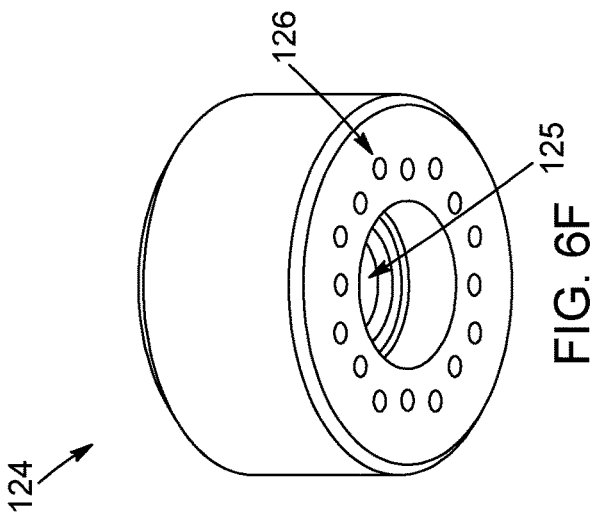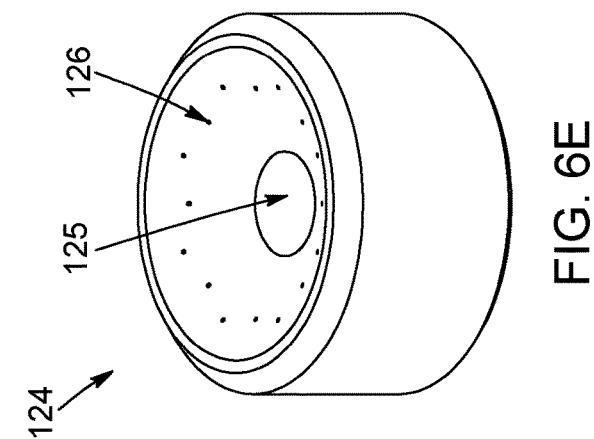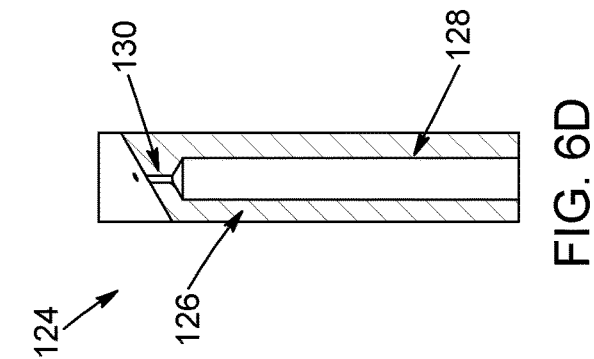

VOLATILE CONTENT MEASUREMENT IN PROCESS STREAMS SUCH AS FROTH TREATMENT TAILINGS

CROSS-REFERENCE TO RELATED APPLICATION

The present application claims priority from Canadian patent application No. CA 3,103,502, filed on Dec. 22, 2020, and entitled "LIGHT HYDROCARBONS CONTENT MEASUREMENT IN BITUMEN-CONTAINING PROCESS STREAMS SUCH AS FROTH TREATMENT TAILINGS", the disclosure of which is hereby incorporated by reference in its entirety.

TECHNICAL FIELD

The technical field generally relates to measurement techniques, and more particularly to measurement techniques for assessing light hydrocarbons content in process streams, such as froth treatment tailings, or the content of other volatile species in process streams.

BACKGROUND

Various types of tailings materials are produced in mining and extraction operations. For example, in oil sands extraction operations, several streams of coarse and fine tailings are produced and are typically supplied to tailings ponds for storage.

One type of tailings material that is produced by bitumen froth treatment contains light hydrocarbons, such as diluent or solvent that was used as part of the bitumen froth treatment process, as well as residual bitumen. In bitumen froth treatment, a light hydrocarbon is added to the bitumen froth in order to enhance the separation of the bitumen components from the aqueous and mineral solids components of the bitumen froth. In naphthenic froth treatment (NFT), the light hydrocarbon is naphtha. In paraffinic froth treatment (PFT), the light hydrocarbon is a paraffinic solvent, such as pentane. In either case, some of the light hydrocarbons report to the underflow tailings streams in the froth treatment process and residual amounts can thus be present in the tailings.

Froth treatment tailings are typically supplied to a tailings pond and therefore the light hydrocarbons can be present in various parts of the tailings pond. Tailings that have been affected by the light hydrocarbons of froth treatment and that are found in the tailings pond can be referred to as froth treatment tailings affected tailings or "FTT affected tailings".

FTT-affected tailings can be further processed to extract residual light hydrocarbons therefrom. Operating parameters of equipment used to perform such further processing of FTT-affected tailings may have to be adjusted depending on the light hydrocarbons content of the input and output streams, among other variables. However, assessing compositional characteristics of process streams associated with the treatment of FTT-affected tailings, such as those that include light hydrocarbons, can pose various challenges given the complex nature of such streams and the low concentration of light hydrocarbons in FTT-affected tailings, among others. For instance, instrumentation used in tailings processing can be prone to fouling and erosion, requiring frequent servicing and cleanup.

As a result, there remain a number of challenges related to the measurement of compositional characteristics of bitumen-containing process streams such as froth treatment tailings.

SUMMARY

In accordance with an aspect, there is provided a method for measuring a volatile content of a process stream comprising volatiles, the method comprising:
  receiving a sample of the process stream into a sample chamber having a chamber volume;
  introducing a stripping gas into the sample of the process stream to strip the volatiles therefrom and produce a gas phase comprising vaporized volatiles;
  detecting the vaporized volatiles in the gas phase to obtain a sample volatile content; and
  determining the volatile content of the process stream based on the sample volatile content.

In some implementations, introducing the stripping gas into the sample of the process stream comprises sparging the stripping gas into the sample.

In some implementations, introducing the stripping gas into the sample of the process stream comprises passing the stripping gas through a perforated plate and then into the sample.

In some implementations, introducing the stripping gas into the sample of the process stream comprises passing the stripping gas through a porous plate and then into the sample.

In some implementations, the stripping gas comprises air.

In some implementations, introducing the stripping gas into the sample of the process stream comprises introducing the stripping gas at a flow rate ranging from about 0.1 L/min. to about 20 L/min.

In some implementations, introducing the stripping gas into the sample of the process stream comprises introducing the stripping gas at a flow rate ranging from about 0.5 L/min. to about 15 L/min.

In some implementations, receiving the sample of the process stream into the sample chamber comprises determining a sample volume of the sample of the process stream.

In some implementations, the chamber volume is a pre-determined chamber volume, and the sample volume is determined relative to the pre-determined chamber volume.

In some implementations, the chamber volume is a pre-determined chamber volume, and the sample volume corresponds to the pre-determined chamber volume.

In some implementations, the chamber volume ranges from about 50 mL to about 1 L.

In some implementations, the chamber volume ranges from about 50 mL to about 500 mL.

In some implementations, receiving the sample of the process stream into the sample chamber comprises flowing the process stream through the sample chamber until a predetermined timepoint is reached, and retaining the sample of the process stream into the sample chamber.

In some implementations, the method further comprises heating the sample of the process stream prior to detecting the vaporized volatiles in the gas phase, to accelerate the stripping of the volatiles therefrom.

In some implementations, heating the sample of the process stream comprises heating the sample of the process stream to a temperature ranging from about 25° C. to about 70° C.

In some implementations, heating the sample of the process stream comprises heating the sample of the process stream to a temperature ranging from about 30° C. to about 50° C.

In some implementations, heating the sample of the process stream comprises heating the sample of the process stream to a temperature ranging from about 35° to about 45° C.

In some implementations, heating the sample of the process stream comprises heating the sample of the process stream to a temperature ranging from about 40° to about 65° C.

In some implementations, the process stream is a hydrocarbon-containing process stream.

In some implementations, the process stream comprises a bituminous process stream.

In some implementations, the process stream comprises dilbit.

In some implementations, the process stream comprises crude oil.

In some implementations, the process stream comprises a refinery-derived process stream.

In some implementations, the process stream is an aqueous process stream comprising mineral solids and water.

In some implementations, the process stream comprises froth treatment tailings.

In some implementations, the froth treatment tailings comprise FTT-affected tailings.

In some implementations, the FTT-affected tailings are retrieved from a tailings pond.

In some implementations, the froth treating tailings are obtained from a froth treatment process.

In some implementations, the process stream is an input stream or an output stream of a light hydrocarbons removal unit.

In some implementations, the light hydrocarbons removal unit comprises a floatation unit configured to remove light hydrocarbons from the FTT-affected tailings.

In some implementations, the light hydrocarbons removal unit comprises a stripping unit configured to remove light hydrocarbons from the FTT-affected tailings.

In some implementations, the process stream is the output stream of the light hydrocarbons removal unit.

In some implementations, the process stream comprises a wastewater stream.

In some implementations, the wastewater stream is from refinery operations.

In some implementations, the volatiles comprise light hydrocarbons.

In some implementations, the light hydrocarbons comprise a naphthenic diluent.

In some implementations, the naphthenic diluent comprises naphtha.

In some implementations, the naphthenic diluent comprises toluene.

In some implementations, the light hydrocarbons comprise a paraffinic solvent.

In some implementations, the paraffinic solvent comprises a $C_3$ to $C_7$ alkane.

In some implementations, the paraffinic solvent comprises propane.

In some implementations, the paraffinic solvent comprises butane.

In some implementations, the paraffinic solvent comprises pentane.

In some implementations, the paraffinic solvent comprises natural gas condensate.

In some implementations, detecting the vaporized volatiles in the gas phase to obtain the sample volatile content comprises measuring the sample volatile content via photoionization.

In some implementations, the volatiles comprise $H_2S$.

In some implementations, detecting the vaporized volatiles in the gas phase to obtain the sample volatile content comprises measuring the sample volatile content via a $H_2S$ sensor.

In some implementations, the process stream is an aqueous process stream.

In some implementations, the process stream comprises a wastewater stream.

In some implementations, the wastewater stream is from refinery operations.

In some implementations, the volatiles comprise $H_2S$.

In some implementations, detecting the vaporized volatiles in the gas phase to obtain the sample volatile content comprises measuring the sample volatile content via a $H_2S$ sensor.

In accordance with another aspect, there is provided a process for measuring a volatile content of a process stream comprising volatiles, the process comprising:

supplying a sample of the process stream to a sample chamber having a chamber volume, the sample chamber being configurable to be in fluid communication with the process stream;

introducing a stripping gas from a stripping gas supply into the sample of the process stream to strip the volatiles therefrom and produce a gas phase comprising vaporized volatiles, the gas phase being receivable in a detection zone in fluid communication with the sample chamber, the detection zone being further configurable to be in fluid communication with the stripping gas supply;

detecting the vaporized volatiles in the gas phase received in the detection zone to obtain a sample volatile content; and determining the volatile content of the process stream based on the sample volatile content.

In some implementations, determining the volatile content of the process stream is performed on-line.

In some implementations, supplying the sample of the process stream to the sample chamber comprises diverting a sub stream of the process stream to the sample chamber, the sample of the process stream corresponding to the sample of the sub stream.

In some implementations, the process further comprises returning the sub stream to the process stream following the diverting of the sub stream of the process stream to the sample chamber and detection of the vaporized volatiles in the gas phase in the detection zone.

In some implementations, returning the sub stream to the process stream comprises, prior thereto, colleting the sub stream in a collection tank in fluid communication with the process stream.

In some implementations, introducing the stripping gas into the sample of the process stream comprises sparging the stripping gas into the sample.

In some implementations, introducing the stripping gas into the sample of the process stream comprises passing the stripping gas through a perforated plate and then into the sample.

In some implementations, introducing the stripping gas into the sample of the process stream comprises passing the stripping gas through a porous plate and then into the sample.

In some implementations, the stripping gas comprises air.

In some implementations, introducing the stripping gas into the sample of the process stream comprises introducing the stripping gas at a flow rate ranging from about 0.1 L/min. to about 20 L/min.

In some implementations, introducing the stripping gas into the sample of the process stream comprises introducing the stripping gas at a flow rate ranging from about 0.5 L/min. to about 15 L/min.

In some implementations, receiving the sample of the process stream into the sample chamber comprises determining a sample volume of the sample of the process stream.

In some implementations, the chamber volume is a pre-determined chamber volume, and the sample volume is determined relative to the pre-determined chamber volume.

In some implementations, the chamber volume is a pre-determined chamber volume, and the sample volume corresponds to the pre-determined chamber volume.

In some implementations, the pre-determined chamber volume ranges from about 50 mL to about 1 L.

In some implementations, the pre-determined chamber volume ranges from about 50 mL to about 500 mL.

In some implementations, the process further comprises heating the sample of the process stream prior to detecting the vaporized volatiles in the gas phase, to accelerate the stripping of the volatiles therefrom.

In some implementations, heating the sample of the process stream comprises heating the sample of the process stream to a temperature ranging from about 25° C. to about 70° C.

In some implementations, heating the sample of the process stream comprises heating the sample of the process stream to a temperature ranging from about 30° C. to about 50° C.

In some implementations, heating the sample of the process stream comprises heating the sample of the process stream to a temperature ranging from about 35° to 45° C.

In some implementations, heating the sample of the process stream comprises heating the sample of the process stream to a temperature ranging from about 40° to 65° C.

In some implementations, detecting the vaporized volatiles in the gas phase to obtain the sample volatile content comprises acquiring a series of successive measured sample volatile contents.

In some implementations, acquiring the series of successive measured sample volatile contents comprises:
  supplying successively a plurality of samples of the process stream to a corresponding plurality of sample chambers;
  introducing the stripping gas successively into the plurality of samples of the process stream to strip the volatiles therefrom and produce a corresponding gas phase comprising vaporized volatiles, the corresponding gas phase being receivable in a corresponding detection zone in fluid communication with a corresponding sample chamber of the plurality of sample chambers; and
  detecting the vaporized volatiles in the corresponding gas phase received in the corresponding detection zone to obtain the series of successive measured sample volatile contents and provide a live volatile content of the process stream.

In some implementations, detecting the vaporized volatiles in the gas phase received is performed during a sampling time ranging from about 1 minute to about 15 minutes.

In some implementations, the sampling time ranges from about 1 minute to about 10 minutes.

In some implementations, the process further comprises purging the detection zone from residual volatiles following the detecting of the vaporized volatiles in the gas phase received in the detection zone to avoid carry-over between samples being analyzed.

In some implementations, purging the detection zone comprises introducing a gas into the detection zone.

In some implementations, purging the detection zone comprises introducing a wash liquid into the detection zone.

In some implementations, the wash liquid comprises water.

In some implementations, the process stream is a hydrocarbon-containing process stream.

In some implementations, the process stream comprises a bituminous process stream.

In some implementations, the process stream comprises dilbit.

In some implementations, the process stream comprises crude oil.

In some implementations, the process stream comprises a refinery-derived process stream.

In some implementations, the process stream is an aqueous process stream comprising mineral solids and water.

In some implementations, the process stream comprises froth treatment tailings.

In some implementations, the froth treatment tailings comprise FTT-affected tailings.

In some implementations, the FTT-affected tailings are retrieved from a tailings pond.

In some implementations, the froth treating tailings are obtained from a froth treatment process.

In some implementations, the process stream is an input stream or an output stream of a light hydrocarbons removal unit.

In some implementations, the light hydrocarbons removal unit comprises a floatation unit configured to remove light hydrocarbons from the FTT-affected tailings.

In some implementations, the light hydrocarbons removal unit comprises a stripping unit configured to remove light hydrocarbons from the FTT-affected tailings.

In some implementations, the process stream is the output stream of the light hydrocarbons removal unit.

In some implementations, the process stream comprises a wastewater stream.

In some implementations, the wastewater stream is from refinery operations.

In some implementations, the volatiles comprise light hydrocarbons.

In some implementations, the light hydrocarbons comprise a naphthenic diluent.

In some implementations, the naphthenic diluent comprises naphtha.

In some implementations, the naphthenic diluent comprises toluene.

In some implementations, the light hydrocarbons comprise a paraffinic solvent.

In some implementations, the paraffinic solvent comprises a $C_3$ to $C_7$ alkane.

In some implementations, the paraffinic solvent comprises propane.

In some implementations, the paraffinic solvent comprises butane.

In some implementations, the paraffinic solvent comprises pentane.

In some implementations, the paraffinic solvent comprises natural gas condensate.

In some implementations, detecting the vaporized volatiles in the gas phase to obtain the sample volatile content comprises measuring the sample volatile content via photoionization.

In some implementations, the volatiles comprise $H_2S$.

In some implementations, detecting the vaporized volatiles in the gas phase to obtain the sample volatile content comprises measuring the sample volatile content via a $H_2S$ sensor.

In some implementations, the process stream is an aqueous process stream.

In some implementations, the process stream comprises a wastewater stream.

In some implementations, the wastewater stream is from refinery operations.

In some implementations, the volatiles comprise $H_2S$.

In some implementations, detecting the vaporized volatiles in the gas phase to obtain the sample volatile content comprises measuring the sample volatile content via a $H_2S$ sensor.

In accordance with another aspect, there is provided a device for measuring a volatile content of a process stream comprising volatiles, the device comprising:
a sample chamber having a chamber volume, the sample chamber being configured for receiving a sample of the process stream;
a stripping gas supply for introducing a stripping gas into the sample of the process stream to strip the volatiles therefrom and produce a gas phase comprising vaporized volatiles, the sample chamber being configured to be alternately in fluid communication with the process stream or with the stripping gas supply; and
a detection zone in fluid communication with the sample chamber to receive the gas phase comprising the vaporized volatiles and to enable measurement of a sample volatile content of the sample that is convertible to the volatile content of the process stream.

In some implementations, the device is installable on-line to provide live monitoring of the volatile content of the process stream.

In some implementations, the device further comprises a sparger downstream of the stripping gas supply to introduce bubbles of the stripping gas into the sample.

In some implementations, the sparger includes openings extending a longitudinal axis of the sparger.

In some implementations, the sparger includes a through hole in a central region thereof.

In some implementations, the openings are distributed around the through hole.

In some implementations, adjacent openings are provided offset to each other.

In some implementations, adjacent openings are equally spaced from each other.

In some implementations, at least one opening of the openings includes first and second concentric holes.

In some implementations, the first concentric hole has a first concentric hole diameter and is located further from the sample chamber than the second concentric hole, and the second concentric hole has a second concentric hole diameter that is larger than the first concentric hole diameter.

In some implementations, a ratio of the second concentric hole diameter relative to the first concentric hole diameter ranges between about ⅓ and about ⅛.

In some implementations, a ratio of the second concentric hole diameter relative to the first concentric hole diameter ranges between about ¼ to about ⅛.

In some implementations, the first concentric hole has a first concentric hole length, and the second concentric hole has a second concentric length, the second concentric length being longer than the first concentric length.

In some implementations, a ratio of the second concentric hole length relative to the first concentric hole length ranges between ⅓ and about ⅑.

In some implementations, a ratio of the second concentric hole length relative to the first concentric hole length ranges between ⅕ and about ⅑.

In some implementations, the sparger is made of a material comprising a polymer.

In some implementations, the polymer is polytetrafluoroethylene.

In some implementations, the device further comprises a perforated plate downstream of the stripping gas supply to introduce bubbles of the stripping gas into the sample.

In some implementations, the device further comprises a porous plate downstream of the stripping gas supply to introduce bubbles of the stripping gas into the sample.

In some implementations, the chamber volume is a pre-determined chamber volume, and the sample volume is determined relative to the pre-determined chamber volume.

In some implementations, the chamber volume is a pre-determined chamber volume, and the sample volume corresponds to the pre-determined chamber volume.

In some implementations, the chamber volume ranges from about 50 mL to about 1 L.

In some implementations, the chamber volume ranges from about 50 mL to about 500 mL.

In some implementations, the sample chamber is provided within a four-way valve.

In some implementations, the sample chamber is configurable in a filling configuration and in a stripping configuration.

In some implementations, the device comprises a rotating structure comprising a channel extending therethrough, the channel defining the sample chamber.

In some implementations, the device valve is configurable in the filling configuration and in the stripping configuration alternatively via rotating of the rotating structure.

In some implementations, in the filling configuration, the device is configured to enable a flow of the process stream flow through the sample chamber.

In some implementations, in the stripping configuration, the sample of the process stream is retained in the sample chamber of the device.

In some implementations, in the stripping configuration, the device is configured to prevent the flow of the process stream through the sample chamber.

In some implementations, in the stripping configuration, the device is configured to enable the stripping gas to flow through the sample chamber.

In some implementations, in the stripping configuration, the sample is retained in the sample chamber and the stripping gas flows through the sample chamber to vaporize the volatiles from the sample of the process stream.

In some implementations, in the stripping configuration, the gas phase is vented to the atmosphere.

In some implementations, the stripping gas supply for introducing the stripping gas into the sample of the process stream is configured to supply the stripping gas at a flow rate ranging from about 0.1 L/min. to about 20 L/min.

In some implementations, the stripping gas supply for introducing the stripping gas into the sample of the process stream is configured to supply the stripping gas at a flow rate ranging from about 0.5 L/min. to about 15 L/min.

In some implementations, the device further comprises a heater operatively connected to the sample chamber and configured to heat the sample of the process stream to accelerate the stripping of the volatiles therefrom prior to detecting the vaporized volatiles in the gas phase.

In some implementations, the heater is configured to heat the sample of the process stream to a temperature ranging from about 25° C. to about 70° C.

In some implementations, the heater is configured to heat the sample of the process stream to a temperature ranging from about 30° C. to about 50° C.

In some implementations, the heater is configured to heat the sample of the process stream to a temperature ranging from about 35° to 45° C.

In some implementations, the heater is configured to heat the sample of the process stream to a temperature ranging from about 45° to 65° C.

In some implementations, the device further comprises a filter provided upstream of the detection zone.

In some implementations, the filter is configured to remove at least one of particles, water droplets and contaminants.

In some implementations, the device further comprises an expander provided upstream of the detection to remove foam generated by the introduction of the stripping gas into the sample of the process stream.

In some implementations, the fluid communication between the detection zone and the sample chamber is provided by a pipeline section, and the expander comprises a portion of the first pipeline section that has a larger diameter than a remaining of the pipeline section.

In some implementations, the device further comprises a detection device to measure the sample volatile content of the gas phase.

In some implementations, the volatiles comprise light hydrocarbons.

In some implementations, the light hydrocarbons comprises a naphthenic diluent.

In some implementations, the naphthenic diluent comprises naphtha.

In some implementations, the naphthenic diluent comprises toluene.

In some implementations, the light hydrocarbons comprise a paraffinic solvent.

In some implementations, the paraffinic solvent comprises a $C_3$ to $C_7$ alkane.

In some implementations, the paraffinic solvent comprises propane.

In some implementations, the paraffinic solvent comprises butane.

In some implementations, the paraffinic solvent comprises pentane.

In some implementations, the paraffinic solvent comprises natural gas condensate.

In some implementations, the detection device comprises a photoionization detector.

In some implementations, the volatiles comprise $H_2S$.

In some implementations, the detection device comprises a $H_2S$ sensor.

In accordance with another aspect, there is provided a process for treating froth treatment tailings that includes bitumen, mineral solids, water, and light hydrocarbons, comprising:
subjecting the froth treatment tailings to light hydrocarbons removal to produce a recovered bitumen froth stream, a light hydrocarbon overhead stream, and a light hydrocarbon-depleted tailings stream;
measuring a light hydrocarbons content of the light hydrocarbon-depleted tailings stream, comprising:
introducing a stripping gas into a sample of the light hydrocarbon-depleted tailings stream to strip the light hydrocarbons therefrom and produce a gas phase comprising vaporized light hydrocarbons;
detecting the vaporized light hydrocarbons in the gas phase to obtain a sample light hydrocarbons content; and
determining the light hydrocarbons content of the light hydrocarbon-depleted tailings stream based on the sample light hydrocarbons content;
controlling the light hydrocarbons removal at least in part based on the light hydrocarbons content of the light hydrocarbon-depleted tailings stream; and
dewatering at least a portion of the light hydrocarbon-depleted tailings stream.

In some implementations, the light hydrocarbons removal is performed in a light hydrocarbons removal unit.

In some implementations, the light hydrocarbons removal unit comprises a floatation unit.

In some implementations, the light hydrocarbons removal unit comprises a stripping unit.

In some implementations, when the light hydrocarbons content of the light hydrocarbon-depleted tailings stream is above a predetermined threshold, the controlling of the light hydrocarbons removal unit is performed such that the light hydrocarbons content of the light hydrocarbon-depleted tailings stream is reduced to be equal or below the predetermined threshold.

In some implementations, the light hydrocarbons removal unit is operated to achieve a target recovery level of the light hydrocarbons from the froth treatment tailings, the target recovery level being determined in accordance with the predetermined threshold of the light hydrocarbons content of the light hydrocarbon-depleted tailings stream.

In some implementations, controlling the light hydrocarbons removal comprises changing at least one operating parameter of the light hydrocarbons removal unit to achieve the target recovery level.

In some implementations, the operating parameter comprises at least one of a froth treatment tailings flow rate as an input stream to the light hydrocarbons removal unit, a light hydrocarbons-depleted tailings stream flow rate as an output stream from the light hydrocarbons removal unit, a residence time of the froth treatment tailings in the light hydrocarbons removal unit, and an impeller speed of an impeller provided within the light hydrocarbons removal unit.

In some implementations, the froth treatment tailings comprises froth treatment tailing (FTT) affected tailings.

In some implementations, the process further comprises retrieving the FTT-affected tailings from a tailings pond.

In some implementations, dewatering the light hydrocarbon-depleted tailings stream comprises:
adding a flocculant to the light hydrocarbon-depleted tailings to produce a flocculated tailings material; and
discharging the flocculated tailings material into a sub-aerial deposition location to allow water to separate from flocculated solid material.

In some implementations, dewatering the light hydrocarbon-depleted tailings stream comprises:
adding an immobilization chemical and a flocculant to the light hydrocarbon-depleted tailings to produce a flocculated tailings material; and supplying the flocculated tailings material into a mine pit to form a permanent aquatic storage structure (PASS) that includes a settled solids-rich layer and a water cap.

In some implementations, the dewatering comprises:
adding a flocculant to the light hydrocarbon-depleted tailings to produce a flocculated tailings material; and
discharging the flocculated tailings material in thin lifts onto a sloped deposition area to allow water to drain away from drying solid material.

In some implementations, measuring the light hydrocarbons content of the light hydrocarbon-depleted tailings stream is performed on-line.

In some implementations, the predetermined threshold is about 1000 wppm.

In some implementations, the predetermined threshold is about 500 wppm.

In some implementations, the predetermined threshold is about 200 wppm.

In some implementations, the light hydrocarbons comprise a naphthenic diluent.

In some implementations, the naphthenic diluent comprises naphtha.

In some implementations, the naphthenic diluent comprises toluene.

In some implementations, the light hydrocarbons comprise a paraffinic solvent.

In some implementations, the paraffinic solvent comprises a $C_3$ to $C_7$ alkane.

In some implementations, the paraffinic solvent comprises propane.

In some implementations, the paraffinic solvent comprises butane.

In some implementations, the paraffinic solvent comprises pentane.

In some implementations, the paraffinic solvent comprises natural gas condensate.

In accordance with another aspect, there is provided a process for treating froth treatment tailings that includes bitumen, mineral solids, water, and light hydrocarbons, comprising:
measuring a light hydrocarbons content of the froth treatment tailings, comprising:
introducing a stripping gas into a sample of the froth treatment tailings to strip the light hydrocarbons therefrom and produce a gas phase comprising vaporized light hydrocarbons;
detecting the vaporized light hydrocarbons in the gas phase to obtain a sample light hydrocarbons content; and
determining the light hydrocarbons content of the froth treatment tailings based on the sample light hydrocarbons content;
subjecting the froth treatment tailings to light hydrocarbons removal in a light hydrocarbon removal unit to reduce the light hydrocarbons content thereof and produce a recovered bitumen froth stream, a light hydrocarbon overhead stream, and a light hydrocarbon-depleted tailings stream; and
controlling an operating parameter of the light hydrocarbons removal based at least in part on the light hydrocarbons content of the froth treatment tailings.

In some implementations, the light hydrocarbons removal is performed in a light hydrocarbons removal unit.

In some implementations, the light hydrocarbons removal unit comprises a floatation unit.

In some implementations, the light hydrocarbons removal unit comprises a stripping unit.

In some implementations, a target recovery level of the light hydrocarbons by the light hydrocarbon removal unit is determined in accordance with the light hydrocarbons content of the froth treatment tailings.

In some implementations, the operating parameter of the light hydrocarbons removal unit is controllable to achieve the target recovery level.

In some implementations, the operating parameter comprises at least one of a froth treatment tailings flow rate as an input stream to the light hydrocarbons removal unit, a light hydrocarbons-depleted tailings stream flow rate as an output stream from the light hydrocarbons removal unit, a residence time of the froth treatment tailings in the light hydrocarbons removal unit, and an impeller speed of an impeller provided within the light hydrocarbons removal unit.

In some implementations, the froth treatment tailings comprises froth treatment tailing (FTT) affected tailings.

In some implementations, the process further comprises retrieving the FTT-affected tailings from a tailings pond.

In some implementations, the light hydrocarbons content of the froth treatment tailings is below about 5000 wppm.

In some implementations, the light hydrocarbons content of the froth treatment tailings is below about 2000 wppm.

In some implementations, the light hydrocarbons content of the froth treatment tailings is below about 1000 wppm.

In some implementations, the process further comprises dewatering at least a portion of the light hydrocarbon-depleted tailings stream.

In some implementations, dewatering the light hydrocarbon-depleted tailings stream comprises:
adding a flocculant to the light hydrocarbon-depleted tailings to produce a flocculated tailings material; and
discharging the flocculated tailings material into a sub-aerial deposition location to allow water to separate from flocculated solid material.

In some implementations, dewatering the light hydrocarbon-depleted tailings stream comprises:
adding an immobilization chemical and a flocculant to the light hydrocarbon-depleted tailings to produce a flocculated tailings material; and
supplying the flocculated tailings material into a mine pit to form a permanent aquatic storage structure (PASS) that includes a settled solids-rich layer and a water cap.

In some implementations, the dewatering comprises:
adding a flocculant to the light hydrocarbon-depleted tailings to produce a flocculated tailings material; and
discharging the flocculated tailings material in thin lifts onto a sloped deposition area as the sub-aerial deposition location to allow water to drain away from drying solid material.

In some implementations, measuring the light hydrocarbons content of the froth treatment tailings is performed on-line.

In some implementations, the light hydrocarbons comprises a naphthenic diluent.

In some implementations, the naphthenic diluent comprises naphtha.

In some implementations, the naphthenic diluent comprises toluene.

In some implementations, the light hydrocarbons comprise a paraffinic solvent.

In some implementations, the paraffinic solvent comprises a $C_3$ to $C_7$ alkane.

In some implementations, the paraffinic solvent comprises propane.

In some implementations, the paraffinic solvent comprises butane.

In some implementations, the paraffinic solvent comprises pentane.

In some implementations, the paraffinic solvent comprises natural gas condensate.

In accordance with another aspect, there is provided a process for treating froth treatment tailings that includes bitumen, mineral solids, water, and light hydrocarbons, comprising:
- subjecting the froth treatment tailings to light hydrocarbons removal in a light hydrocarbon removal unit to reduce the light hydrocarbons content thereof and produce a recovered bitumen froth stream, a light hydrocarbon overhead stream, and a light hydrocarbon-depleted tailings stream;
- measuring a light hydrocarbons content of a tailings material present in the light hydrocarbon removal unit, comprising:
  - introducing a stripping gas into a sample of the tailings material to strip the light hydrocarbons therefrom and produce a gas phase comprising vaporized light hydrocarbons;
  - detecting the vaporized light hydrocarbons in the gas phase to obtain a sample light hydrocarbons content; and
  - determining the light hydrocarbons content of the tailings material based on the sample light hydrocarbons content; and
- controlling an operating parameter of the light hydrocarbons removal unit based at least in part on the determined light hydrocarbons content of the tailings material.

In accordance with another aspect, there is provided a process for treating a bitumen-containing stream that includes bitumen and light hydrocarbons, comprising:
- subjecting the bitumen-containing stream to light hydrocarbons removal in a light hydrocarbon removal unit to reduce the light hydrocarbons content thereof and produce a light hydrocarbon overhead stream, and a light hydrocarbon-depleted stream;
- measuring a light hydrocarbons content of a process fluid selected from the group consisting of the bitumen-containing stream, the light hydrocarbon-depleted stream, and a bitumen-containing material present within the light hydrocarbon removal unit, the measuring comprising:
  - introducing a stripping gas into a sample of the process fluid to strip the light hydrocarbons therefrom and produce a gas phase comprising vaporized light hydrocarbons;
  - detecting the vaporized light hydrocarbons in the gas phase to obtain a sample light hydrocarbons content; and
  - determining the light hydrocarbons content of the process fluid based on the sample light hydrocarbons content; and
- controlling an operating parameter of the light hydrocarbons removal unit based at least in part on the determined light hydrocarbons content of the process fluid.

In accordance with another aspect, there is provided a method for measuring a volatile content of a process stream comprising volatiles, the method comprising:
- receiving a sample of the hydrocarbon-containing process stream into a sample chamber having a chamber volume;
- introducing a stripping gas into the sample of the process stream to strip the volatiles therefrom and produce a gas phase comprising vaporized volatiles;
- detecting the vaporized volatiles in the gas phase to obtain a sample volatile content; and
- determining the volatile content of the process stream based on the sample volatile content.

In some implementations, introducing the stripping gas into the sample of the process stream comprises sparging the stripping gas into the sample.

In some implementations, receiving the sample of the process stream into the sample chamber comprises flowing the process stream through the sample chamber until a predetermined timepoint is reached, and retaining the sample of the process stream into the sample chamber.

In some implementations, the volatiles comprise light hydrocarbons.

In some implementations, the light hydrocarbons comprise naphtha, toluene, light aromatic compounds, C3 to C7 aliphatic compounds, natural gas condensate, or a combination thereof.

In some implementations, detecting the vaporized volatiles in the gas phase to obtain the sample volatile content comprises measuring the sample volatile content via photoionization.

In some implementations, the volatiles comprise $H_2S$, and detecting the vaporized volatiles in the gas phase to obtain the sample volatile content comprises measuring the sample volatile content via a $H_2S$ sensor.

In some implementations, the method further comprises heating the sample of the process stream prior to detecting the vaporized volatiles in the gas phase, to accelerate the stripping of the volatiles therefrom.

In some implementations, the process stream comprises a wastewater stream.

In some implementations, the wastewater stream comprises refinery wastewater.

In some implementations, the process stream comprises a process stream derived from refinery operations.

In accordance with another aspect, there is provided a process for producing a hydrocarbon product, comprising:
- treating a feedstock to produce the hydrocarbon product and an associated process stream;
- measuring a volatile content of the associated process stream, comprising:
  - supplying a sample of the associated process stream to a sample chamber having a chamber volume, the sample chamber being configurable to be in fluid communication with the associated process stream;
  - introducing a stripping gas from a stripping gas supply into the sample of the associated process stream to strip the volatiles therefrom and produce a gas phase comprising vaporized volatiles, the gas phase being receivable in a detection zone in fluid communication with the sample chamber, the detection zone being further configurable to be in fluid communication with the stripping gas supply;
  - detecting the vaporized volatiles in the gas phase received in the detection zone to obtain a sample volatile content; and
  - determining the volatile content of the associated process stream based on the sample volatile content.

In some implementations, the process further comprises measuring the volatile content of the hydrocarbon product.

In some implementations, treating the feedstock comprises refining and the hydrocarbon product comprises a refinery-derived product.

In some implementations, the process further comprises adjusting the treating of the feedstock based on the volatile content of the hydrocarbon product or of the associated process stream.

In some implementations, the associated process stream comprises a wastewater stream.

In some implementations, the wastewater stream comprises refinery wastewater and the hydrocarbon product comprises a refinery-derived product.

In some implementations, the associated process stream comprises froth treatment tailings, the hydrocarbon product comprises diluted bitumen, and the feedstock comprises oil sands material.

In some implementations, the volatiles comprise light hydrocarbons.

In accordance with another aspect, there is provided a device for measuring a volatile content of a process stream comprising volatiles, the device comprising:
- a sample chamber having a chamber volume, the sample chamber being configured for receiving a sample of the process stream;
- a stripping gas supply for introducing a stripping gas into the sample of the process stream to strip the volatiles therefrom and produce a gas phase comprising vaporized volatiles, the sample chamber being configured to be alternately in fluid communication with the process stream or with the stripping gas supply;
- a detection zone in fluid communication with the sample chamber to receive the gas phase comprising the vaporized volatiles; and
- a detection device extending within the detection zone to measure a sample volatile content of the sample that is convertible to the volatile content of the process stream.

In some implementations, the device is installable on-line to a pipeline through which the process stream flows, to provide live monitoring of the volatile content of the process stream.

In some implementations, the device further comprises a sparger downstream of the stripping gas supply to introduce bubbles of the stripping gas into the sample.

In some implementations, the device further comprises a heater operatively connected to the sample chamber and configured to heat the sample to accelerate the stripping of the volatiles therefrom prior to detecting the vaporized volatiles in the gas phase.

In some implementations, the detection device comprises a photoionization system configured to measure the volatile content when the volatiles comprise light hydrocarbons.

It is noted that various implementations of the methods, processes and devices described above can include additional features and aspects described herein.

BRIEF DESCRIPTION OF THE DRAWINGS

FIG. 6A is a top view of a sparger of a volatile content measuring device, the sparger including a plurality of openings.

FIG. 6B is a bottom view of the sparger shown in FIG. 6A.

FIG. 6C is a cross-sectional view of the sparger shown in FIG. 6A.

FIG. 6D is a cross-sectional view of a detail of the sparger shown in FIG. 6A, showing an opening including first and second concentric holes provided successively.

FIG. 6E is a top perspective view of the sparger shown in FIG. 6A

FIG. 6F is a bottom perspective view of the sparger shown in FIG. 6A

DETAILED DESCRIPTION

Figure 1:
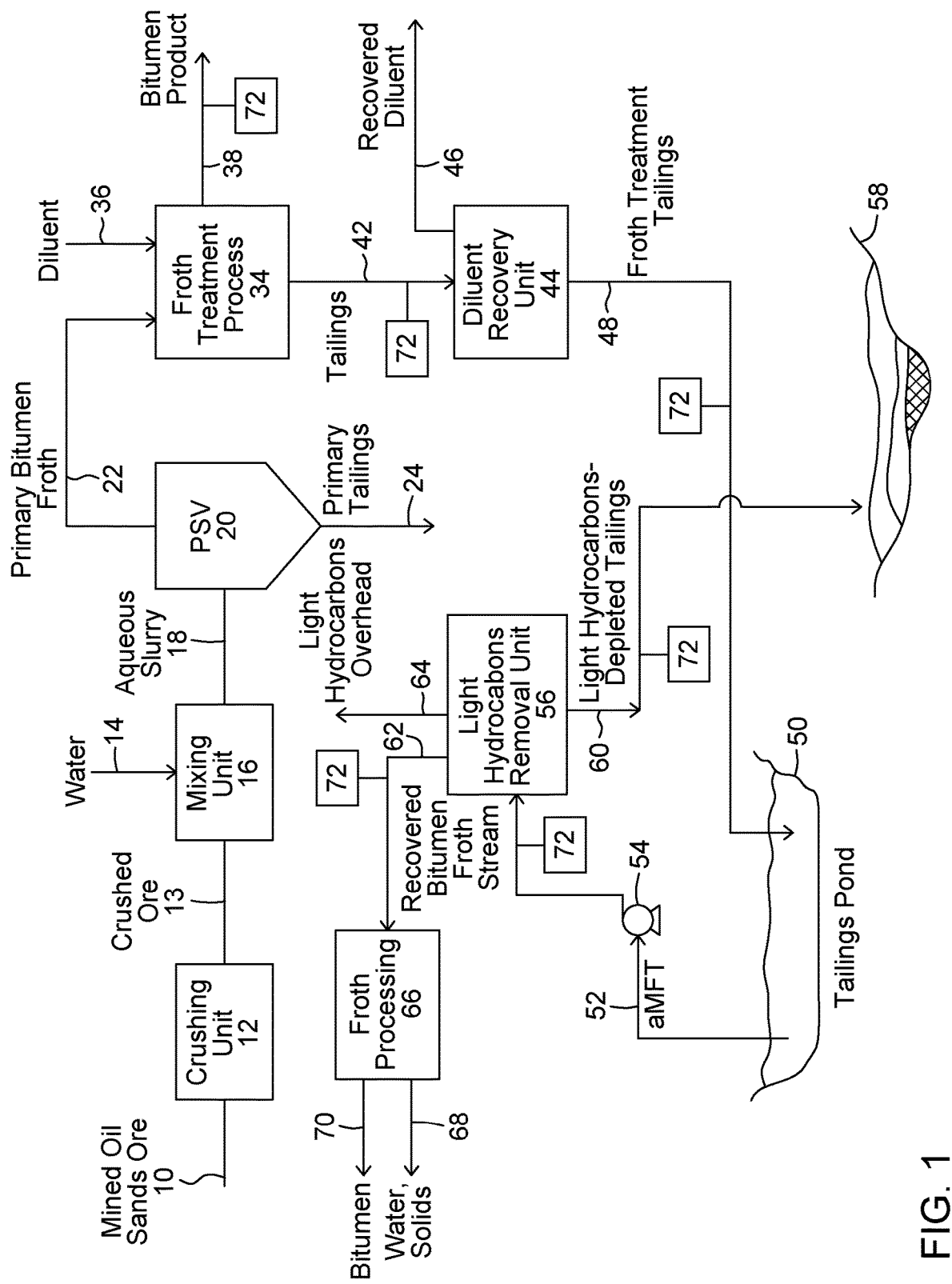
FIG. 1 is a process flow diagram illustrating an overview of a bitumen recovery process that includes the production of froth treatment tailings that are discharged in a tailings pond, and subsequent treatment of FTT-affected tailings in a light hydrocarbons removal unit to produce light hydrocarbons-depleted tailings.

Techniques described herein relate to devices and methods for measuring a volatile species content in process streams. The process streams can include multiphase process streams, such as process streams associated with the management of Froth Treatment Tailings (FTT) affected tailings, which can be referred to as FTT-affected tailings, process streams associated with froth treatment operations, and process streams associated with refineries, such as refinery wastewater. These types of process streams generally include an aqueous phase and a hydrocarbon phase, with volatile species such as light hydrocarbons and hydrogen sulfide ($H_2S$) that can be dispersed in the hydrocarbon phase or in the aqueous phase, respectively. When hydrocarbons are present in the process stream, such process stream can be referred to as a hydrocarbon-containing process stream. Additional examples of process streams can include for instance crude oil, bitumen or dilbit, as will be explained in more detail below.

The described techniques take advantage of the low boiling point of the volatiles that can be present in such process streams to measure a content of the volatiles following their vaporization and separation from a given process stream. In some implementations, the described techniques can therefore be viewed as corresponding to a stripping process resembling those implemented to remove residual light hydrocarbons from FTT-affected tailings, for instance, although the stripping can take place "on-line" as a miniaturized stripping process to measure the content of vaporized volatiles, such as light hydrocarbons and/or $H_2S$, in a finite space having a measurable volume.

The techniques can include receiving a sample of the process stream for which determination of a volatile content is desired into a sample chamber. As mentioned above, the sample chamber can have a measurable volume such that the content of the volatiles, which can be for instance a naphtha content or a $H_2S$ content, can be assessed in that measurable volume, which can range for instance from 10 mL to 1 L. A stripping gas, such as air, is introduced into the sample of the process stream, for instance via a sparger, to vaporize the volatiles contained in the sample. The introduction of the stripping gas results in the production of a gas phase comprising vaporized volatiles and the stripping gas, and enables the separation of the vaporized volatiles from the sample of the process stream. A concentration of the vaporized volatiles in the gas phase is then measured using a detection device, which can be for instance a photoionization detector or a $H_2S$ sensor, which in turn provides the content of light hydrocarbons or $H_2S$ in the sample tested, respectively. Once the volatile content of the sample is known, the volatile content of the sample can be correlated to the volatile content of the process stream, for instance by performing back calculations.

Many challenges are typically associated with the measurement of concentrations of volatiles in process streams, such as process streams associated with bitumen froth treatment and with the management of tailings, refinery wastewater streams, and process streams associated with refinery operations. For instance, froth treatment streams and tailings streams are generally complex mixtures of water, solids, bitumen and light hydrocarbons, and very few on-line or at-line analytical instruments are robust enough against this type of multiphase aqueous mixture. It is to be noted that when referring to a multiphase aqueous mixture, it is meant to refer to a mixture that includes at least about 50 vol. % of water. However, this definition can vary depending on the type of mixture, and is used herein as a general indication of the composition of the mixture. In addition, the light hydrocarbons content in such process streams can typically be below 5000 ppm, or below 0.5 wt %, which can make it difficult to measure under field conditions. Furthermore, since volatiles such as light hydrocarbons are generally dissolved in the bitumen phase, conventional instrumentation has to allow sufficient time to let the light hydrocarbons be released from the bitumen phase in order to detect a representative concentration of light hydrocarbons, which can also put further constraints on the instrumentation.

It may also be desirable to measure a volatile content of a process stream associated with refinery operations, such as crude oil, or dilbit, which may not be easily feasible using conventional instrumentation. Examples of drawbacks associated with the use of conventional instrumentation can include fouling, and the difficulty of using optical instruments given the opaque nature of crude oil and its complex composition. For instance, evaluating the light hydrocarbons content of a crude oil stream used as feedstock for a fractionation column can provide valuable insights regarding the composition of the crude oil stream, with can in turn be assessed against the outputs of the fractionation column. It may also be desirable to control the amount of diluent, such as naphtha, that is added to bitumen to produce dilbit to ensure that the dilbit is within pipelinable specifications without adding too much of diluent, which could have economical drawbacks. Similarly, measuring the light hydrocarbons content of a refinery feed stream such as dilbit may be useful information for a refinery operator for controlling downstream separation processes. Furthermore, measuring $H_2S$ can be important in order to meet product specification, to protect equipment from corrosion and for environmental and safety concerns.

The methods and devices described herein can be beneficial for performing volatile content measurements of "live" process streams such as froth treatment tailings streams, de-aerated froth, wastewater streams, dilbit, bitumen, crude oil and other refinery-derived process streams, and for concentrations of volatiles in the analyzed process streams that are below 0.5 wt %, which can be done independently of processing conditions and variables such as pressure, light hydrocarbons-to-bitumen ratio, and composition of the process stream. In turn, measurements of volatile content can be beneficial to control and adjust operating parameters of the process to which is subjected the analyzed process stream. In other implementations, the concentration of the volatiles in the analyzed process streams can be at least 0.5 wt %. Alternatively, the concentration of the volatiles can be expressed in ppm. For instance, when $H_2S$ is measured, concentrations of $H_2S$ that can range for example from about 50 ppm to 1000 ppm, or about 50 ppm to about 500 ppm, can be measured. In other implementations, concentrations outside of that example range can also be measured, for instance concentrations below about 50 ppm or above about 1000 ppm.

General Overview of a Bitumen Recovery Process, and Associated Generation and Treatment of FTT Affected Tailings Referring to FIG. 1, in a primary extraction operation, oil sands ore 10 is mined and crushed in a crushing unit 12 to obtain a crushed ore 13. The crushed ore 13 is mixed with water 14 in a mixing unit 16, such as a rotary breaker, to form an aqueous slurry 18 comprising bitumen. The aqueous slurry 18 is then conditioned to prepare the bitumen for separation from the aqueous slurry 18. The conditioning can be performed for instance by transportation of the aqueous slurry 18 from one location to another. The aqueous slurry 18 is subsequently supplied to a primary separation vessel 20, also referred to as a PSV, for separation into primary bitumen froth 22 and primary tailings 24. The primary tailings 24 can be further treated or be deposited in a tailings pond for settling. The primary separation vessel 20 can also produce a middlings stream that can be supplied to a secondary separation vessel (not shown), which in turn can produce a secondary bitumen froth that can be supplied back to the primary separation vessel 20 or combined with the primary bitumen froth 22. The secondary separation vessel can also produce secondary tailings.

The primary bitumen froth 22 is then fed to a froth treatment process 34, wherein the primary bitumen froth 22 is diluted with a diluent 36 to obtain a diluted bitumen froth. The diluent 36 can be either a naphthenic type diluent or a paraffinic type diluent. The naphthenic type diluent can for example include toluene, naphtha or other light aromatic compounds. The paraffinic type diluent can for example include $C_3$ to $C_7$ aliphatic compounds and/or natural gas condensate. The froth treatment process 34 separates the diluted bitumen froth into a bitumen product 38 and tailings 42. The froth tailings 42 can be further treated in a diluent recovery unit 44 to recover a portion of the diluent 36 therefrom as recovered diluent 46, and produce froth treatment tailings 48. The froth treatment tailings 48 can then be deposited in a froth treatment tailings pond 50 for settling.

A tailings stream can be retrieved 52 from the tailings pond 50. The tailings stream can be retrieved from a mature fine tailings (MFT) layer of the tailings pond 50. The tailings stream 52 can be referred to as FTT-affected tailings, affected MFT, "aMFT", or FTT-affected fluid tailings, for example, as these tailings have been affected by the light hydrocarbons of froth treatment. A pump 54 can be used to retrieve the affected MFT 52 from the tailings pond 50 and supply the affected MFT 52 to a light hydrocarbons removal unit 56. The pump could also be a dredge or a barge.

While the FTT-affected tailings 52 that are supplied to the light hydrocarbons removal unit 56 are typically from an MFT layer of a tailings pond, they can also be sourced from other FTT-affected tailings sources and could include or consist of FTT supplied directly from the froth treatment operation. The tailings that are fed into the light hydrocarbons removal unit 56 can be any combination of FTT, FTT-affected tailings, and other tailings materials that contain or are affected by light hydrocarbons. It is also noted that tailings not affected by light hydrocarbons can be combined with the affected tailings to form the tailings stream fed to the light hydrocarbons removal unit 56.

As mentioned above, residual light hydrocarbons, such as those present in a naphthenic type diluent or a paraffinic type diluent, can remain in froth treatment tailings that are produced during bitumen froth treatment processes. The light hydrocarbons found in FTT-affected tailings 52 can undesirably support microbial activity and generate $CH_4$, $CO_2$, and $H_2S$, and can therefore have an impact or alter aquatic closure performance as well as add to greenhouse gas and volatile organic compound emissions. It may therefore be beneficial to remove these light hydrocarbons present in the affected MFT 52, for instance in a light hydrocarbons removal unit 56 such as the one illustrated in FIG. 1, to improve the composition of the FTT-affected tailings 52. Once treated, the FTT-affected tailings 52 may become more suitable for permanent containment of the materials, such as in a permanent aquatic storage structure, or "PASS" 58, where dewatering and consolidation occur over time.

As used herein, the expression "light hydrocarbons" can be interpreted as corresponding to any hydrocarbon or mixture of hydrocarbons that is light enough to be vaporized to a gas phase from a liquid phase using a stripping gas such as air, at conditions that would not vaporize heavier hydrocarbons such as bitumen or heavy oil therefrom. For instance, the expression "light hydrocarbons" can refer to residual light hydrocarbons that can be present in process streams such as froth treatment tailings. In some implementations, the light hydrocarbons can include naphtha, toluene, light aromatic compounds, $C_3$ to $C_7$ aliphatic compounds or natural gas condensate. Naphtha, which is an upgrader product that can be used as a diluent in various parts of a bitumen extraction process, can include a mixture of hydrocarbons in the $C_1$ to $C_{10}$ range, and in the context of the present description, can be considered as a mixture of light hydrocarbons.

The light hydrocarbon removal unit 56 can include various types of separation units to separate light hydrocarbons from the affected FTT 52. For instance, in some implementations, the light hydrocarbon removal unit 56 can include a floatation unit, a stripping unit, or both, or can include any other types of units that enable recovery of light hydrocarbons from FTT-affected tailings. When the light hydrocarbon removal unit 56 includes both a floatation unit and a stripping unit, the floatation unit and the stripping unit can be provided sequentially in any order.

The light hydrocarbons removal unit 56 produces light hydrocarbons-depleted tailings 60, a recovered bitumen froth stream 62, and a vapour overhead stream 64 comprising light hydrocarbons. In some implementations, the recovered bitumen stream 62 can be subjected to froth processing 66 to separate one or more of its various components, including bitumen, water, solids, and diluent. The froth processing 66 can include one or more separators that remove water and solids 68 from the recovered bitumen froth stream 62 in order to produce an upgraded bitumen froth 70 that is suitable for reintroduction into the froth treatment process 34 of the main oil sands processing plant. It should be noted that the froth processing 66 can also be adapted depending on the type of light hydrocarbons that are present in the tailings that are treated. The light hydrocarbons-depleted tailings 60 having a reduced content in light hydrocarbons compared to the MFT-affected tailings 52 treated in the light hydrocarbons removal unit 56 may then be subjected to dewatering, which can include discharging the light hydrocarbons-depleted tailings 60 into a permanent aquatic storage structure 58 as described above.

There are various types of dewatering operations that exist that can be used for separating water from the mineral solids contained in the light hydrocarbons-depleted tailings 60. In one example, the dewatering operation includes adding an immobilization chemical to the light hydrocarbons-depleted tailings 60 followed by a flocculant in order to produce a flocculated tailings material, which is then conditioned in a pipeline and supplied to the permanent aquatic storage structure 58. In the permanent aquatic storage structure 58, the flocculated solids with immobilized contaminants of concern settle to the bottom to form a settled solids layer, and a water cap forms as an upper layer of the permanent aquatic storage structure 58.

It is also noted that alternative dewatering processes can also be used. For example, in one dewatering process a flocculant solution can be added to the cleaned tailings in order to produce a flocculated tailings material which can then be pipeline conditioned and deposited in thin lifts on a sloped sub-aerial deposition area in order to form a dry tailings material and allowing the water to drain and flow away from the drying solids. Various other dewatering processes can also be used and can involve filters, thickeners, deposition methods, and various other techniques.

The performance of the light hydrocarbons removal unit 56 can depend, at least in part, on the measurement of the light hydrocarbons content of the MFT-affected tailings 52 that form the feed stream that is supplied to the light hydrocarbons removal unit 56 as an input stream, and/or on the measurement of the light hydrocarbons content of the light hydrocarbons-depleted tailings 60 that forms the output stream from the light hydrocarbons removal unit 56. Such measurement(s) can be beneficial to assess the quality of the light hydrocarbons-depleted tailings 60 for determining its suitability for storage in a permanent aquatic storage structure 58 for dewatering, and for controlling the operating parameters of the light hydrocarbons removal unit 56. In some implementations, it may also be desirable to measure the light hydrocarbons content of the MFT-affected tailings present within the light hydrocarbons removal unit 56.

Accordingly, the light hydrocarbons removal unit 56 can be operated to achieve a given target of a light hydrocarbons content in the light hydrocarbons-depleted tailings 60, i.e., such that the light hydrocarbons content in the light hydrocarbons-depleted tailings 60 is below a predetermined threshold. In some implementations, the light hydrocarbons removal unit 56 can be operated such that the predetermined threshold for the light hydrocarbons content of the light hydrocarbons-depleted tailings 60 is less than about 1000 ppm, less than about 500 ppm, less about 400 ppm, less than about 300 ppm, less than about 200 ppm, or less than about 100 ppm. In some implementations, the predetermined threshold of the light hydrocarbons content in the light hydrocarbons-depleted tailings 60 can be determined according to the dewatering process to be used.

In addition, since the light hydrocarbons content of MFT-affected tailings in a tailings pond can vary considerably, the configuration or design of the light hydrocarbons removal unit 56 can require adjusting processing conditions based on the extent of light hydrocarbons removal desired, which can be facilitated by the availability of on-line measurements of light hydrocarbons on the feed stream of MFT-affected tailings 52 and/or on the light hydrocarbons-depleted tailings 60. The availability of on-line measurements of the light hydrocarbons content of the feed stream of MFT-affected tailings 52 and of the light hydrocarbons content of the light hydrocarbons-depleted tailings 60 can also enable designing the light hydrocarbons removal unit 56 based on an average light hydrocarbons content instead of being designed to treat a maximum light hydrocarbons content of the tailings ponds at a constant feed flow rate, which can undesirably lead to increased operational costs.

In some implementations, the light hydrocarbons removal unit 56 can be operated to achieve a target recovery level of the light hydrocarbons from the MFT-affected tailings 52, and the target recovery level can be determined so as to meet the predetermined threshold of the light hydrocarbons content of the light hydrocarbon-depleted tailings stream 60.

As mentioned above, the MFT-affected tailings 56 can have a variable composition, in terms of bitumen content, solids content, and light hydrocarbons content. In some implementations, the MFT-affected tailings 56 can include between 5 wt % and 15 wt % of solids, between 80 wt % and 90 wt % of water, and between 1 wt % and 5 wt % of bitumen. These concentrations can be variable depending on the tailings ponds and on the characteristics of the froth treatment tailings 48 being discharged in the tailings ponds. The light hydrocarbons removal unit 56 can thus be configured to manage such variations in the composition of the feed stream in order to meet a given specification of light hydrocarbons content of the light hydrocarbons-depleted tailings 60. In some implementations, the extent of light hydrocarbons removal can depend on the residence time in the light hydrocarbons removal unit 56, and the flow rate of the feed stream can be controlled based on the light hydrocarbons content of the feed stream, which can enable reducing the size of the light hydrocarbons removal unit 56. The bitumen content of the MFT-affected tailings 52 can also vary significantly, such that the amount of bitumen in the recovered bitumen froth stream 62 that is recovered from the light hydrocarbons removal unit 56 can be a function of the bitumen content of the feed stream and the flow rate into the light hydrocarbons removal unit 56.

Still referring to FIG. 1, a volatile content measuring device 72 can be provided at various locations across the bitumen recovery process. As mentioned above, in some implementations, it can be beneficial to implement on-line light hydrocarbons content measurements upstream of the light hydrocarbons removal unit 56 and/or downstream of the light hydrocarbons removal unit 56. When the volatile content measuring device 72 is provided downstream of the light hydrocarbons removal unit 56, the volatile content measuring device 72 can be provided to measure a light hydrocarbons content of the light hydrocarbons-depleted tailings 60 or of the recovered bitumen froth stream 62, or both. The choice of the location where the volatile content measuring device 72 is provided can depend on the objective for assessing the light hydrocarbons content. For instance, if it is desired to obtain information on the light hydrocarbons content of the light hydrocarbons-depleted tailings prior to discharge into a permanent aquatic storage structure, the volatile content measuring device 72 can be provided on such stream. If it is desired to obtain information on the residual light hydrocarbons content of the recovered bitumen froth stream 62, then the volatile content measuring device 72 can be provided on such stream. Either one of these assessments can influence the operation of the light hydrocarbons removal unit 56, and the operating parameters of the light hydrocarbons removal unit 56 can be adjusted accordingly to achieve a given removal threshold of the light hydrocarbons from the input steam, i.e., the tailings stream 52. Examples of variables of the light hydrocarbon removal unit 56 that can be adapted taking into consideration the results of the light hydrocarbons measurements can include the impeller speed of an impeller provided in the light hydrocarbons removal unit 60, the flow rate at which the light tailings stream 52 is supplied to the light hydrocarbon removal unit 56, the flow rate at which the light hydrocarbons-depleted tailings 60 is retrieved from the light hydrocarbon removal unit 56, the residence time of the light hydrocarbons-depleted tailings 60 in the light hydrocarbon removal unit 56, and the flow rate of a stripping fluid being introduced into the light hydrocarbon removal unit 56, when the light hydrocarbon removal unit 56 includes a floatation unit or a stripping unit.

Alternatively, or in addition to the measurement of the light hydrocarbons content of the various process streams described above, the volatile content measuring device 72 can be used to measure the content of one or more volatile species such as $H_2S$.

To perform measurements of a volatile content on the MFT-affected tailings present in the light hydrocarbons removal unit 56, a side stream can be retrieved from the light hydrocarbon removal unit 56 via a sampling line, and the volatile content measuring device 72 can be provided on the sampling line and operated as described herein.

It is to be understood that any process stream that contains volatiles such as light hydrocarbons or $H_2S$ can also be assessed. For instance, it may be desirable to measure the content of light hydrocarbons in the froth treatment tailings 48 from the diluent recovery unit 44 prior to discharge to a tailings ponds 50 to ensure that it is below a certain level. Such assessment can be indicative of the performance of the diluent recovery unit 44. Information can also be gathered regarding the light hydrocarbons content of the input stream to the diluent recovery unit 44, i.e., the stream of tailings 42.

Another example of a process stream that can be assessed for volatile content such as light hydrocarbon content or $H_2S$ content can be the bitumen product 38 produced by the froth treatment process 34, which can include diluent that has been added to the primary bitumen froth 22 to be subjected to the froth treatment process 34. In this scenario, information collected via the volatile content measuring device 72 can be useful to determine the composition of the bitumen product 28.

In some implementations, it may also be desirable to measure the volatile content of an aqueous process stream other than tailings streams, such as wastewater streams from various sources. For example, wastewater streams from refinery operations can be analyzed with the volatile content measuring device 72 to assess a light hydrocarbon content and/or a $H_2S$ content.

Other examples of process streams that can be assessed for volatile content can include process stream that have a reduced content of water and solids compared to tailings, or that do not include water or solids. For instance, the volatile content measuring device 72 can be used in the context of partial upgrading processes that include separating a light fraction from a heavier fraction of a hydrocarbon feedstock, in order to measure a light hydrocarbons content of the light fraction. The volatile content measuring device 72 can also be used for distillation applications.

Yet other examples of process streams that can be assessed for volatile content can include crude oil or other refinery-derived products (also referred to as refinery-derived process streams), and bituminous streams such as dilbit and de-aerated froth, e.g., bitumen froth from a primary separation vessel or a secondary separation vessel that has been subjected to de-aeration to remove air therefrom.

Furthermore, in the context of the present description, certain process streams can be referred to as hydrocarbon products. For instance, in some implementations, refinery-derived products such as crude oil can be considered as hydrocarbon products. In such implementations, the hydrocarbon product can be obtained by treating a feedstock, such as a by refining a feedstock, which can also produce an associated process stream such as a wastewater stream, e.g., refinery wastewater. In other implementations, the feedstock can include crude oil, and the hydrocarbon product can be the output of a distillation column or a fractionation column that produces refinery-derived products such as diesel, kerosene, etc., which can also produce an associated process stream such as a wastewater stream, e.g., refinery wastewater. Another example of a hydrocarbon product can be a bitumen product, such as diluted bitumen, i.e., dilbit. In such implementations, the hydrocarbon product can be obtained by treating a feedstock that comprises an oil sands material. In such implementations, the treating of the feedstock can produce an associated process stream, such as a wastewater stream or froth treatment tailings.

It is to be understood that any process stream that has a low enough viscosity to allow a flow of gas bubbles to flow through a sample of the process stream to strip volatile species contained therein, such as light hydrocarbons and $H_2S$, can be suitable for implementing the volatile content measuring device 72 as described herein. The process stream being assessed may or may not contain hydrocarbons. When the process stream includes hydrocarbons, such process stream can be referred to as a hydrocarbon-containing process stream. A hydrocarbon-containing process stream as used herein can contain various proportions of hydrocarbons. For example, the hydrocarbon-containing process stream can include hydrocarbons in a proportion that ranges from trace amounts of hydrocarbons to hydrocarbon-containing process streams that contains at least a majority of hydrocarbons. Thus, a hydrocarbon-containing process stream as used herein can be considered as corresponding to any process stream that contains at least traces amounts of hydrocarbons.

Example Implementation of a Volatile Content Measuring Device

Process Stream: Froth Treatment Tailings

Figure 2A:
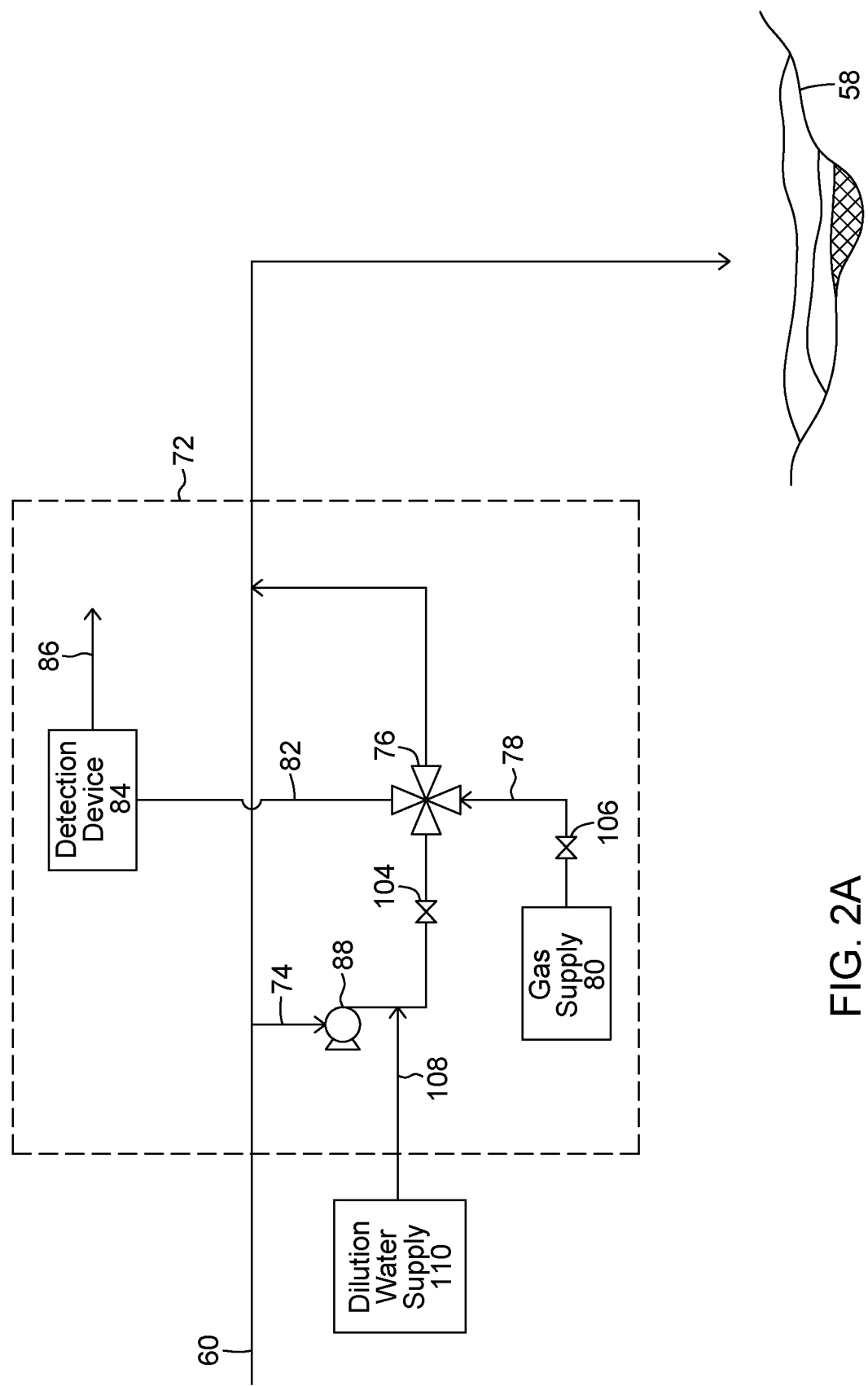
FIG. 2A is a process flow diagram illustrating an implementation of a volatile content measuring device installed on-line.
Figure 2B:
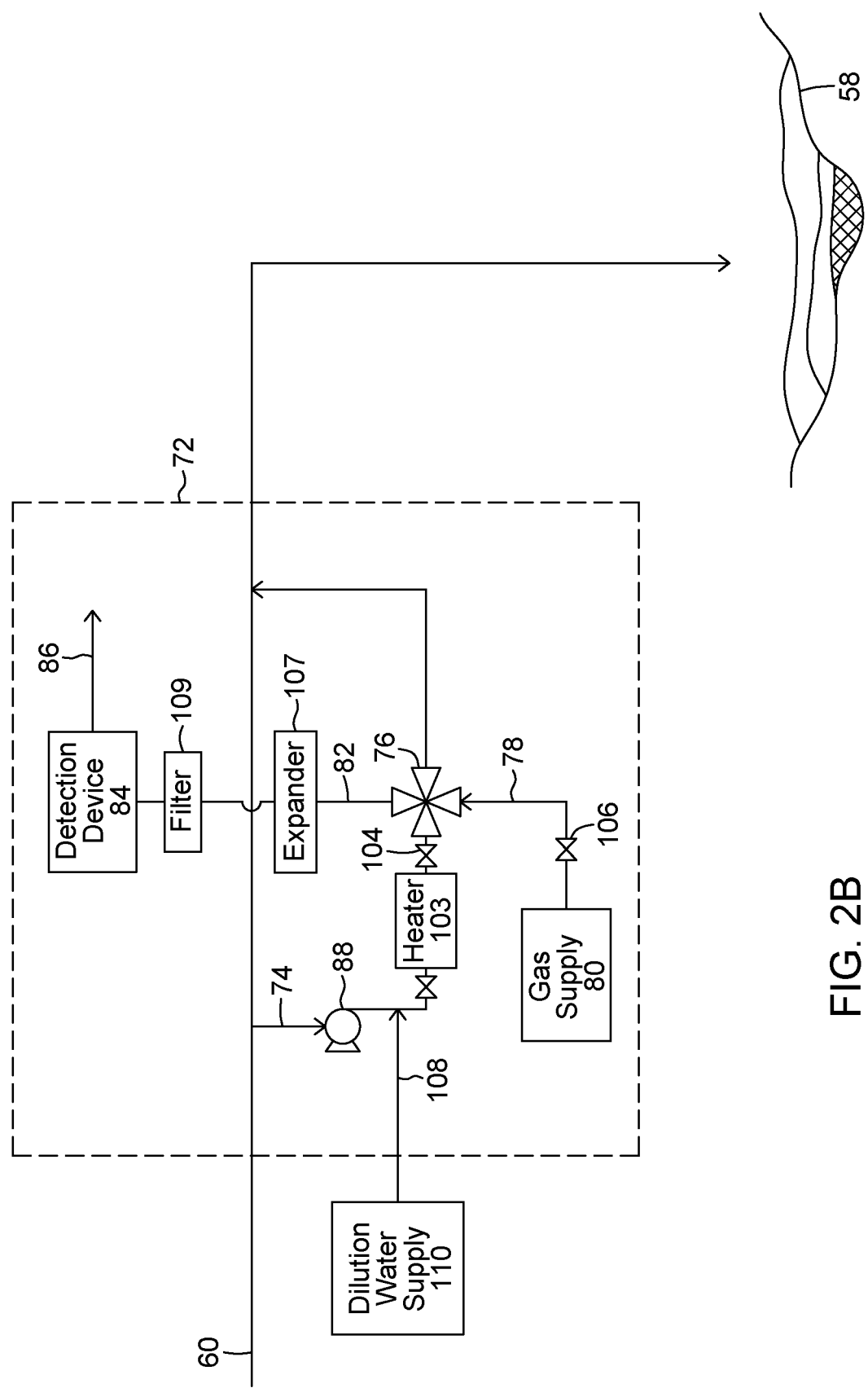
FIG. 2B is a process flow diagram illustrating another implementation of a volatile content measuring device installed on-line, with the volatile content measuring device including a heater, an expander and a filter.

Turning now to FIGS. 2A and 2B, an example of an on-line implementation of the volatile content measuring device 72 is shown. In this implementation, the volatile content measuring device 72 is illustrated as being provided in fluid communication with the stream of light hydrocarbons-depleted tailings 60 that is produced by the light hydrocarbons removal unit 56. The stream of light hydrocarbons-depleted tailings 60 is shown as being supplied via pipeline to another location, such as a permanent aquatic storage structure 58. A portion of the stream of light hydrocarbons-depleted tailings 60 is diverted, also via pipeline, as a sub-stream 74 of the light hydrocarbons-depleted tailings 60 to the volatile content measuring device 72.

Although a single volatile content measuring device 72 is shown as being provided along the pipeline transporting the sub stream 74 of the light hydrocarbons-depleted tailings 60, a plurality of volatile content measuring devices 72 can also be provided in parallel along the pipeline transporting the sub stream 74 of the light hydrocarbons-depleted tailings 60 to obtain a series of measurements that are representative of the light hydrocarbons content of the light hydrocarbons-depleted tailings 60. Additional details regarding this aspect are provided below.

The volatile content measuring device 72 can include a sample chamber for receiving a sample of a process stream, a stripping gas supply for introducing a stripping gas into the sample of the process stream to strip the volatiles therefrom and produce a gas phase comprising vaporized volatiles, and a detection zone in fluid communication with the sample chamber to receive the gas phase that includes the vaporized volatiles to enable measurement of a sample volatile content of the sample that is convertible to the volatile content of the process stream. The sample chamber is configurable to alternatively be in fluid communication with the process stream and with the stripping gas supply.

It is to be understood that when referring to a volatile content of a process stream, the volatile content measure device 72 can be configured to measure the content of one or more volatiles, with corresponding detection devices being provided to measure the selected volatiles. For instance, in some implementations, the volatile content can include a light hydrocarbons content, and the detection device 84 can be configured to measure the light hydrocarbons content of the sample of the process stream. In other implementations, the volatile content can include a $H_2S$ content, and the detection device 84 can be configured to measure the $H_2S$ content of the sample of the process stream. In yet other implementations, the volatile content can include a light hydrocarbons content and a $H_2S$ content, and the detection device 84 can include a first detection device to measure the light hydrocarbons content of the sample of the process stream, and a second detection device to measure the $H_2S$ content of the sample of the process stream. Thus, any number of volatile contents can be determined in the gas phase of the sample of the process stream in accordance with the detection devices provided to do so.

In the illustrated implementation, the volatile content measuring device 72 includes a four-way valve 76, and the sample chamber is provided by the four-way-valve 76. The volatile content measuring device 72 is designed to adopt at least two configurations: a first configuration that enables a flow of the sub-stream 74 of light hydrocarbons-depleted tailings 60 through the sample chamber, and a second configuration that prevents the flow the sub-stream 74 of light hydrocarbons-depleted tailings 60 to flow through the sample chamber but enables flow of the stripping gas therethrough. It is important to note that although the volatile content measuring device 72 is described in the following paragraphs as including a four-way valve 76, any other structure that enables receiving a known volume of a sample of the process stream analyzed in a sample chamber and subjecting the sample to stripping with a stripping gas to produce a vaporized gas phase can be suitable. Thus, the principles described below with regard to the volatile content measuring device 72 and associated four-way valve 76 can be applied more broadly to any structure that can be configured to receive a known volume of a sample of the process stream and to enable subjecting the sample to stripping with a stripping gas to produce a vaporized gas phase, such as a structure defining a sample chamber that is provided with valves to allow successive introduction of the sample in the sample chamber and of the striping gas into the sample chamber. Accordingly, although the embodiments of the volatile content measuring device 72 and corresponding parts thereof, such as the four-way valve 76, are describe as having certain geometrical configurations as explained and illustrated herein, not all of these components and geometries are essential and thus should not be taken in their restrictive sense. It is to be understood, as also apparent to a person skilled in the art, that other suitable components and cooperation therebetween, as well as other suitable geometrical configurations, can be used for the volatile content measuring device 72, as can be easily inferred by a person skilled in the art.

As mentioned above, in the first configuration, the volatile content measuring device 72 can be configured such that the flow of the sub-stream 74 of light hydrocarbons-depleted tailings 60 can flow through the sample chamber, which can be provided by a four-way valve 76, and subsequently join the main stream of the light hydrocarbons-depleted tailings 60, as illustrated in FIGS. 2A and 2B. In some implementations, a collection tank (shown in FIG. 5) can be provided downstream of the volatile content measuring device 72 and upstream of the main stream of the light hydrocarbons-depleted tailings 60 to collect the sub-stream 74 prior to the sub-stream 74 being combined with the main stream of the light hydrocarbons-depleted tailings 60. Returning the sub stream 74 to the main stream of the light hydrocarbons-depleted tailings 60 can be beneficial to avoid having to manage the disposal of an additional tailings stream.

In some implementations, the flow rate of the sub-stream 74 of light hydrocarbons-depleted tailings can range from about 0.1 $m^3$/h to about 5 $m^3$/h, while the flow rate of the main stream of the light hydrocarbons-depleted tailings 60 can range from about 1000 $m^3$/h to about 3000 $m^3$/h. It is to be noted that these values are for example only, and that other flow rates are possible, for instance depending on the process for which the volatile content measurements are desired.

In the second configuration, the volatile content measuring device 72 can be configured to prevent the sub-stream 74 of light hydrocarbons-depleted tailings 60 to flow through the sample chamber, and can rather define a passage for a stripping gas 78 that is supplied from a gas supply 80 to flow through the sample chamber. When the volatile content measuring device 72 is in the second configuration and the sample chamber is provided by a four-way valve 76, the stripping gas 78 can be introduced into a sample of the sub stream 74 of the light hydrocarbons-depleted tailings 60 that is retained within a cavity of the four-way valve 76 to vaporize volatiles therefrom, such as light hydrocarbons and/or $H_2S$, and produce a gas phase 82. The gas phase 82 is analyzed by a detection device 84 that is configured to detect a concentration of the volatiles that are present in a given volume of the gas phase 82. Once quantitative measurements of the concentration of the volatiles present in the given volume of the gas phase 82 have been taken, the gas phase 82 can be vented as a vent stream 86. In addition, once quantitative measurements of the concentration of the volatiles present in the given volume of the gas phase stream 82 have been taken, the four-way valve 76 can return to the first configuration to once again enable passage of the sub stream 74 of the light hydrocarbons-depleted tailings 60 therethrough. In some implementations, a pump 88 can be provided to facilitate circulation of the sub stream 74 through the four-way valve 76 and subsequent combination with the main stream of the light hydrocarbons-depleted tailings 60.

When in the first configuration, a valve 104 provided on the pipeline configured to supply the sub stream 74 to the sample chamber of the volatile content measuring device 72 can be operated to prevent the flow of the sub steam 74 to the sample chamber of the volatile content measuring device 72. When in the second configuration, a valve 106 provided on the line configured to supply the stripping gas 78 to the sample chamber of the volatile content measuring device 72 from the gas supply 80 can be operated to prevent the stripping gas 78 to reach the sample chamber of the volatile content measuring device 72.

Referring to FIG. 2B, optionally, the volatile content measuring device 72 can further include a heater 103 upstream of the four-way valve 76 to heat the sub stream 74 prior to the sub-stream 74 of light hydrocarbons-depleted tailings 60 being introduced into the sample chamber. Heating the sub-stream 74 of light hydrocarbons-depleted tailings 60 can subsequently facilitate stripping and vaporization of the volatiles to the gas phase 82, and decrease the residence time of the sample of sub stream 74 in the sample chamber. The decrease in residence time can increase the throughput and sampling frequency for a given volatile content measuring device 72 thus increasing the data produced by each, which in turn can reduce the number of volatile content measuring devices 72 needed to achieve a given sampling frequency. An additional valve can optionally be provided on the pipeline configured to supply the sub stream 74 to the four-way valve 76, upstream of the heater 103.

Still referring to FIG. 2B, optionally, the volatile content measuring device 72 can further include an expander 107 provided on a pipeline section, referred to hereinbelow as a stripping gas pipeline section 95, that carries the gas phase 82 away from the four-way valve 76. The expander 107 can be a portion of the pipeline section that has a larger cross-section, e.g., a larger diameter, compared to upstream or downstream thereof. The presence of the expander 107 on the pipeline section can facilitate the removal of foam that can potentially be generated during the introduction of the stripping gas into the sample of the sub stream 74. Thus, the expander 107, can contribute to protect the detection device 84 from such foam, which could otherwise damage the detection device or lead to inaccurate measurements by the detection device 84.

Still referring to FIG. 2B, optionally, the volatile content measuring device 72 can further include a filter 109 can also be provided on the stripping gas pipeline section 95 that carries the gas phase 82 away from the four-way valve 76, downstream of the four-way valve 76 or of the expander 107 if present, and upstream of the detection device 84. The filter 109 can be configured to remove particles, water droplets or undesirable contaminants that can potentially remain in the gas phase 82, to protect the detection device 86 and prevent inaccurate measurements by the detection device 84.

Additional details will now be provided regarding the operation of the four-way valve 76 and the associated detection device 84, with the process stream being exemplified as the light hydrocarbons-depleted tailings 60 from mature froth treatment tailings described above.

Figure 4:
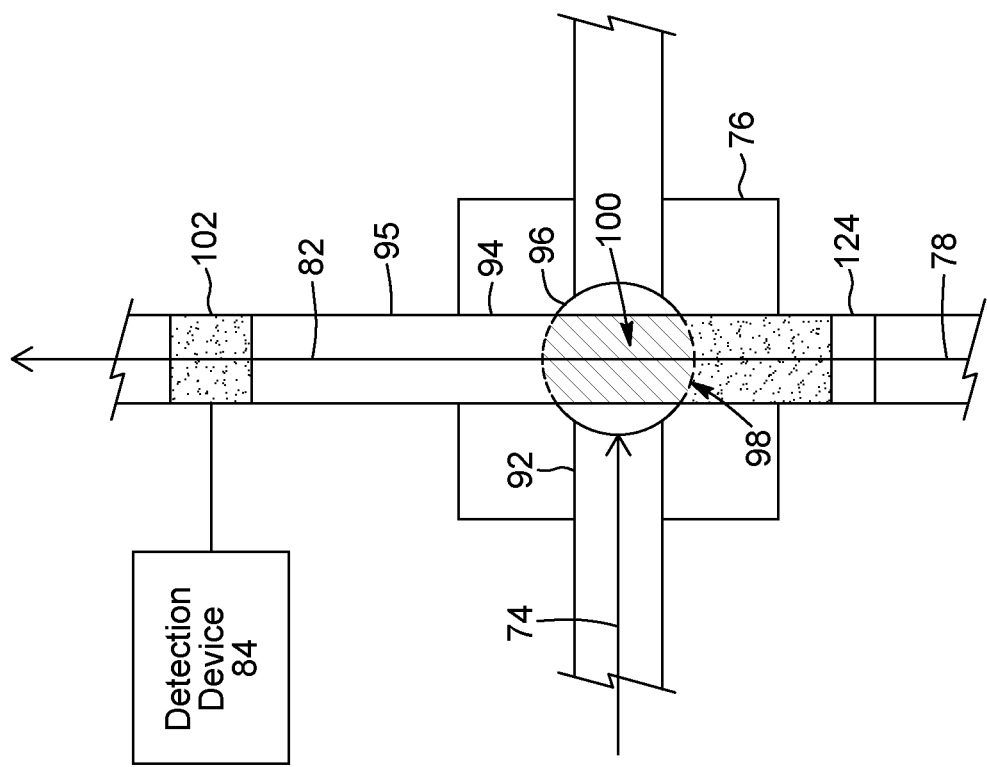
FIG. 4 is a schematic representation of a cross-section of a volatile content measuring device shown in a stripping configuration.
Figure 3:
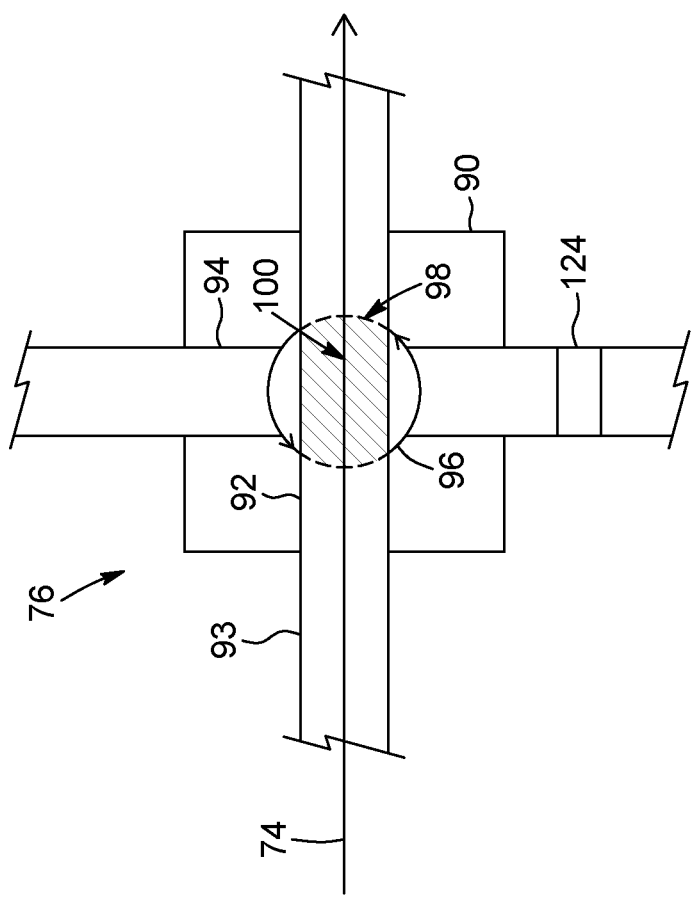
FIG. 3 is a schematic representation of a cross-section of a volatile content measuring device shown in a filling configuration.

FIG. 3 illustrates an implementation of the four-way valve 76 shown in the first configuration, and FIG. 4 illustrates an implementation of the four-way valve 76 shown in the second configuration. The four-way valve 76 includes a valve body 90, a first channel 92 and a second channel 94.

The first channel 92 is configured to receive the sub stream 74 of the light hydrocarbons-depleted tailings 60, and is in fluid communication with a sub stream pipeline section 93 that transports the sub stream 74. The second channel 94 is configured to receive the stripping gas 78, and is in fluid communication with a stripping gas pipeline section 95 that supplies the stripping gas 78 to the four-way valve 76, or that carries the gas phase 82 away from the four-way valve 76. The four-way valve 76 further includes a rotating structure 96 that includes a third channel 98 extending therethrough. In some implementations, the rotating structure 96 can correspond to the ball of the four-way valve 76. The expression "third channel" can also be considered to refer to a bore or a ball cavity of a four-way valve, as known in the art.

When the four-way valve 76 is in the first configuration such as shown in FIG. 3, the third channel 98 aligns with the first channel 92 to let the sub stream 74 of the light hydrocarbons-depleted tailings 60 flow therethrough. Thus, in the first configuration, the first channel 92 and the third channel 98 are aligned to form a substantially continuous channel that extends through the body 90 of the four-way valve 76.

Furthermore, the third channel 98 defines a sample chamber 100 having a finite and pre-determined volume. In some implementations, the sample chamber 100 can be sized to accommodate a volume of sample from which a volatile content can be derived. The volume of sample chamber can range for instance from about 50 mL to about 1 L, or from about 50 mL to about 500 mL. Other volumes are also possible, and can be determined based on the characteristics of the process stream being analyzed. For example, in some implementations, volatile content measurements on a sample that is substantially homogenous can be performed on a smaller sample volume compared to a sample that is less homogenous, or inhomogeneous.

Thus, in FIG. 3, the sample chamber 100 of the volatile content measuring device 72 is exemplified as corresponding to the "third channel" of the four-way valve 76, which can be the bore or the ball cavity of the four-way valve 76. However, it is to be understood that the sample chamber of the volatile content measuring device 72 can be defined by a structure other than a four-way valve, as mentioned above.

Turning now to FIG. 4, in the second configuration, the rotating structure 96 of the four-way valve 76 has been rotated 90° from its position in the first configuration, such that the sample chamber 100 becomes in fluid communication with the second channel 94. As the rotating structure 96 is rotated, a sample of the sub stream 74 of the light hydrocarbons-depleted tailings 60 remains within the sample chamber 100, the sample being represented by the shaded area within the rotating structure 96. Considering the composition of the light hydrocarbons-depleted tailings 60, which typically includes between 5 wt % and 15 wt % of solids, between 80 wt % and 90 wt % of water, and between 1 wt % and 5 wt % of bitumen, and the temperatures and pressures at which is operated the volatile content measuring device 72, the sample of the sub stream 74 of the light hydrocarbons-depleted tailings 60 is generally considered to be in liquid phase.

The sample of the sub stream 74 of the light hydrocarbons-depleted tailings 60 has a measurable volume. For instance, in some implementations, the volume of the sample can correspond to the volume of the sample chamber 100, assuming that the sample substantially fills the sample chamber 100.

In the second configuration, the sample chamber 100 forms a continuous channel with the second channel 94. In such a configuration, the sample of the sub stream 74 of the light hydrocarbons-depleted tailings 60 is in fluid communication with the gas supply 80, such that the stripping gas 78 can be introduced into the sample of the sub stream 74 of the light hydrocarbons-depleted tailings 60.

The stripping gas 78 can be air, or any other suitable gas that can be used for stripping volatiles. The stripping gas 78 can be free of hydrocarbons to minimize interference with the measurement of the volatile content in the sample being analyzed. If volatiles are present, their known amount can be subtracted from the volatile measurements performed on the sample of the sub steam 74.

The sub stream 74 of the light hydrocarbons-depleted tailings 60 can be transported via pipeline to the four-way valve 76 under turbulent regime such that the sample that is taken from the sub stream 74 and that is retained in the sample chamber 100 can be considered substantially homogenous and representative of the overall composition of the light hydrocarbons-depleted tailings 60. It is to be understood that non-homogeneity within the sample retained in the sample chamber 100 can also occur, and would not alter the measurement of the concentration of volatiles in that sample.

As the stripping gas 78 is introduced into the sample of the sub stream 74 of the light hydrocarbons-depleted tailings 60, the stripping gas 78 strips the volatiles that are dispersed in the liquid sample of the sub stream 74, and volatiles are vaporized therefrom to form the gas phase 82 that includes vaporized volatiles and stripping gas 78. The stripping gas 78 can be introduced into the sample of the sub stream 74 of the light hydrocarbons-depleted tailings 60 via a sparger 124 that positioned normally, or transversally, with regard to a longitudinal axis of the second channel 94. Alternatively, a perforated plate or a porous plate can be provided normally, or transversally, with regard to a longitudinal axis of the second channel 94 to produce bubbles of stripping gas 78 that is supplied from the gas supply 80.

Referring to FIGS. 6a to 6F, and example of a sparger 124 that can be installed across the second channel 94 is shown. The sparger 124 includes a through hole 125 in a central region thereof, and includes a plurality of openings 126 extending therethrough, along a longitudinal axis of the sparger 124, and around the through hole 125. In the implementation shown, adjacent openings 126 are provided offset to each other, with a first one 126a of the adjacent openings 126 being closer to the outer periphery of the sparger compared to a second one 126b of the adjacent openings 126. Furthermore, in the implementation shown, the openings 126 are equally spaced from each other. It is to be understood that different distributions of the openings 126 are also possible, and that the openings 126 can be provided according to a given pattern if desired.

Referring more particularly to FIGS. 6C and 6D, the opening 126 includes first and second concentric holes 128, 130 provided successively. The first concentric hole 128 is the one that would be provided furthest away from the four-way valve once the sparger 124 is installed on the stripping gas pipeline section 95, and the second hole 130 is the one that would be provided closest to the four-way valve once the sparger 124 is installed on the stripping gas pipeline section 95. In other words, the second concentric hole 130 is provided downstream of the first concentric hole 128 when the sparger 124 is in use. The second concentric hole 130 has a diameter, i.e., a second concentric hole diameter, that is smaller than a diameter of the first concentric hole 128, i.e., a first concentric hole diameter. The decrease in the diameter from the first concentric hole 128 to the second concentric hole can increase the flow rate of the stripping gas 78 flowing in the stripping gas pipeline section 95, which in turn can facilitate introduction of the stripping gas 78 into the sample of the sub stream 74 of the light hydrocarbons-depleted tailings 60. The ratio of the second concentric hole diameter relative to the first concentric hole diameter can vary. For instance, in the implementation shown, the ratio the second concentric hole diameter relative to the first concentric hole diameter is about 1/6. In other implementations, the ratio the second concentric hole diameter relative to the first concentric hole diameter can range between about 1/3 to about 1/8. The length of each of the first and second concentric holes 128, 130 can also vary. For instance, in the implementations shown, the ratio of the length of the second concentric hole 130 relative to the length of the first concentric hole 128 is about 1/7. In other implementations, the ratio of the length of the second concentric hole 130 relative to the length of the first concentric hole 128 can range from about 1/3 to about 1/9. In some implementations, the sparger 124 can be made of a polymer, such as polytetrafluoroethylene (PTFE). In some implementations, the sparger 124 can be configured to generate gas bubbles having a substantially uniform size across the sample chamber, which in turn can contribute to increase the accuracy of the measurements subsequently taken by the detection device 84.

In light of the above, the first configuration can also be referred to as a filling configuration since it allows the passage of the sub stream of light hydrocarbons-depleted tailings 60 therethrough to fill the cavity of the four-way valve 76, and the second configuration can be referred to as a stripping configuration, since it prevents the passage of the sub stream 74 of the light hydrocarbons-depleted tailings 60 therethrough but enables passage of the stripping gas 78 therethrough to strip the light hydrocarbons from the sample of the sub stream 74 of the light hydrocarbons-depleted tailings 60.

In some implementations, the use of a four-way valve 76 can be beneficial to provide a positive displacement sampling technique characterized by a continuous displacement of the sub stream 74 through the first channel 92 and the sample chamber 100 when the four-way valve 76 is in the filling configuration, which in turn enables the discrete sampling of a representative sample of the sub stream 74 having a measurable volume once the four-way valve 90 is switched to the stripping configuration.

The detection device 84 is provided to measure a concentration of the vaporized volatiles in the gas phase 82 in a detection zone 102, which is shown arbitrarily on FIG. 4 as a section of the stripping gas pipeline section 95 located downstream of the four-way valve 76. In some implementations, the detection device 84 can be configured to measure a light hydrocarbons content in the gas phase 82 present in the detection zone 102. In such implementations, the detection device 84 can be configured to detect concentrations of light hydrocarbons ranging from about 5 wppm to about 5000 wppm, from between 10 wppm to about 2000 wppm, or from between 10 wppm to about 1000 wppm, on a whole sample basis. It is to be noted that these ranges are only examples of certain concentrations of light hydrocarbons that can be detected by the detection device associated with the volatile content measuring device 72, which of course can vary depending on the detection device used and the configuration of the volatile content measuring device 72. Furthermore, in other implementations and as mentioned above, the detection device 84 can be configured to measure the $H_2S$ content in the gas phase 82 present in the detection zone 102. In yet other implementations, the detection device 84 can include a first detection device to measure the light hydrocarbons content in the gas phase 82 present in the detection zone 102, and a second detection device to measure the $H_2S$ content in the gas phase 82 present in the detection zone 102. When first and second detection devices are provided, the sparging force used to introduce the stripping gas 78 into the sample of the sub stream 74 that is retained in the sample chamber 100 can be determined in accordance with the type of volatiles for which a volatile content is desired to be obtained. For instance, the sparging force can be chosen to ensure that the volatile having a higher stripping threshold can effectively be stripped. In some implementations, when it is desired to measure both a light hydrocarbons content and a $H_2S$ content, the sparging force can be determined to ensure that the light hydrocarbons are stripped, as the light hydrocarbons can have a higher stripping threshold than $H_2S$. The sparging force can be varied for instance by adjusting a flow rate of the stripping gas that is introduced into the sample and/or by modifying the configuration of the sparger 124, with a higher flow rate of the stripping gas resulting in a higher stripping force and vice versa.

Thus, any number of volatile contents can be determined in the gas phase of the sample of the process stream in accordance with the detection devices provided to do so. When more than one detection device is provided to measure a given volatile content in the detection zone 102, the detection device can be placed one after the other, in series, or the detection devices can be arranged to face each other on either side of the detection zone 102. Alternatively, when it is desired to use more than one detection device 84, a corresponding number of volatile content measuring devices 72 can be provided to be operated in parallel, each having a dedicated detection device 84.

In some implementations, formation of foam can undesirably contribute to gas holdup in the sample. A gas disengagement zone can be provided downstream of the four-way valve 76 and upstream of the detection zone 102. The gas disengagement zone can contribute to avoid formation of foam in the sample. The gas disengagement zone can also be provided as an addition in the length to the stripping gas pipeline section 95 downstream of the four-way valve 76 to avoid foam, if formed, to reach the detection device 84. The gas disengagement zone can be configured for instance as a pipeline section that is made of nylon, followed by another pipeline section that is made of stainless steel. Such configuration can facilitate reducing fouling issues that may arise downstream of the four-way valve 76. When a gas disengagement zone is provided in addition to an expander 107, the gas disengagement zone can be located upstream of the expander 107, with the expander 107 removing remaining foam if present. Alternatively, the gas disengagement zone can be located downstream of the expander 107 to remove foam that can remain following passage through the expander 107.

In some implementations, the detection device 84 can include a photoionization detector. In such implementations, a sample of the gas phase 82 is bombarded with ultraviolet (UV) radiation in the vacuum ultraviolet range, i.e., within a 10-200 nm wavelength. Radiation in this region is ionizing, as it has enough energy to cause the ejection of an electron in a compound. The amount of energy required for the ejection of an electron to occur is compound specific, as quantified by the ionization potential of the molecule analyzed. If the energy provided by the photoionization detector is greater than the ionization potential of the molecule, an electron will be ejected, producing a positively charged ion.

By passing these through an electric field, the number of charged particles, which is related to the initial concentration of the molecules from which they have been ejected, can be quantified through measurement of the electric current produced by the charged particles.

The use of a photoionization detector can be beneficial since the type of measurement performed by a photoionization detector is not compound-specific. In other words, any molecules having ionization energies less than that of the UV source can have an impact on the signal. Since the light hydrocarbons present in the gas phase 82 can be a mixture of various hydrocarbons, it can be challenging to assign a single concentration to such sample. For instance, when the light hydrocarbons removal unit 56 is configured to remove diluent such as naphtha from affected tailings 52, naphtha includes various hydrocarbons within the $C_1$ to $C_{10}$ range and other interfering compounds. The ionization potentials of the compounds in naphtha are typically <10 eV, which are less than those of potentially interfering compounds such as oxygen (13.6 eV), and nitrogen (24 eV). Therefore, by using a UV source of ~10.6 eV for the photoionization detector, light hydrocarbons of interest can be discriminated from other interfering compounds in the sample of gas phase 82 that is analyzed. In the case of naphtha, the species in naphtha can be discriminated from the non-naphtha species in the sample of gas phase 82 that is analyzed.

In some implementations, water vapour may be present in the gas phase 82 produced by the stripping of the sample that is analyzed. Since water absorbs photons, the presence of water vapour can lead to an undesirable quenching phenomenon. To remedy this quenching phenomenon, the photoionization detector can include a Teflon membrane on the inlet of the device, the membrane being sized to exclude water. In this configuration, the sample of gas phase 82 that is analyzed can be periodically drawn through the membrane, at relatively short intervals.

The use of a photoionization detector can thus enable detection of the concentration of light hydrocarbons, such as naphtha in the sample of gas phase 82 that is analyzed. Considering that only water and light hydrocarbons are expected to be volatile under measurement conditions, the measurements techniques described herein can be considered as being independent of the temperature at which are taken the measurements, the composition of the process stream from which is taken the sample to be analyzed other than the light hydrocarbons being measured, and of the flow rate of the stripping gas 78.

In other implementations, the detection device 84 can include a $H_2S$ sensor. Examples of $H_2S$ sensors include those measuring changes in electrical resistance based on a chemical reaction that occurs when $H_2S$ passes or enters the sensor. Any other type of $H_2S$ sensor can also be suitable. When the volatile content measured is a $H_2S$ content, temperature and pH corrections may be required to improve measurement accuracy. Measuring a $H_2S$ content can provide various benefits, such as maintaining the process stream assessed within a given specification, characterizing the quality of the process stream, for instance when the process stream is dilbit or the like, or to monitor acid gas formation during extraction of bitumen from oil sands.

The flow rate at which the stripping gas 78 is transported into the second channel 94 and introduced into the sample of the sub stream 74 that is retained in the sample chamber 100 can vary. For example, in some implementations, the flow rate of the stripping gas 78 can range for instance from about 0.1 L/min. to about 20 L/min., or from about 0.5 L/min. to about 15 L/min.

In some implementations, the pressure of the stripping gas 78 within the second channel 94 and the sample chamber 100 can be close to ambient pressure. In other implementations, the pressure of the stripping gas 78 within the second channel 94 and the sample chamber 100 can be higher than ambient pressure.

The concentration of volatiles measured by the detection device 84 can be tracked with time and at a pre-determined timepoint determined by a data processing algorithm, calculations can be performed to convert the concentration of the volatiles in the measurable volume of the sample that was stripped to a concentration of volatiles in the sample in liquid phase. The concentration of volatiles of the sample in liquid phase can then be interpreted as corresponding to the volatiles concentration in the sub stream 74.

Once the four-way valve 76 has gone through a stripping cycle, which would correspond to the four-way valve 76 being initially in the first configuration to fill the sample chamber 100 with a sample of the sub stream 74, and subsequently switched to the second configuration during which the stripping gas 78 is introduced into the sample, the four-way valve 76 can be switched back to the first configuration to allow the sub stream 74 to circulate therethrough again.

During stripping, volatiles volatilize according to their vapour pressure. In some implementations, the sub stream 74 can be heated to increase the vapour pressure of the volatiles and accelerate the stripping of the light hydrocarbons from the sample. For instance, the sub stream 74 can be heated to a temperature ranging from about 25° C. to about 70° C., from about 30° C. to about 50° C., from about 35° to 45° C., or from about 40° C. to about 65° C.

Referring back to FIGS. 2A and 2B, in some implementations, dilution water 108 from a dilution water supply 110 may be added to the sub stream 74 to provide a desired rheology for the process stream to facilitate stripping of volatiles therefrom. For instance, in scenarios where the sub stream 74 includes more than about 30 wt % of solids, or more than about 20 wt % of solids, dilution water 108 may be added to reduce the solids content of the sub stream 74 and thus the sample to be analyzed to below about 15 wt % of solids, or below about 10 wt % of solids.

In some implementations, the second channel 94 and the sample chamber 100 can be cleaned with wash water or another wash solution to remove residual tailings that may be present, when the process stream includes tailings. Following the wash solution flush, air can also be introduced into the second channel 94 and the sample chamber 100 to dry the line out, and to purge the detection zone 102 from residual gas phase volatiles that may still be present. In addition, the detection device 84 can also be relied upon to indicate that the concentration of volatiles in the detection zone 102 has returned to baseline levels, after which a next sample of the sub stream 74 can be analyzed.

In some implementations, stripping gas 78 may become trapped in the sampling chamber 100, such as when the four-way valve 76 is switched back from the second configuration to the first configuration. To address this possibility, a vent port may be provided into a top portion of the four-way valve 76, allowing the trapped air to escape when re-configuring the four-way valve 76 from the second configuration to the first configuration and allowing the sub stream 74 to flow therethrough again. In some implementations, the amount of stripping gas 78 trapped in the sample chamber 100 can also be minimized by increasing the flow rate at which the sub stream 74 is circulated through the first channel 92 and the sample chamber 100. In other words, the flow rate at which the sub stream 74 is circulated through the first channel 92 and the sample chamber 100 when the four-way valve 76 is in the first configuration can be determined to avoid stripping gas 78 being trapped in the sample chamber 100.

Determination of the Volatile Content of the Process Stream

The evaluation of the content of volatiles in a process stream, such as a tailings stream, as described herein is based on rationalizing the quantity of volatiles that is stripped to the mass of the sample that is collected in the sample chamber 100. The configuration shown in FIGS. 3 and 4 is designed to collect a repeatable volume of material, i.e., of a process stream, using the sample chamber 100, or ball cavity, of the four-way valve 76. In some implementations, it can be assumed that the solids content in the light hydrocarbons depleted-tailings 60 may not exhibit significant variability, which can imply that the density of the light hydrocarbons depleted-tailings 60 can remain substantially constant. As a result, sampling a repeatable volume of the process stream is expected to correspond to the sampling of a repeatable mass of the sample.

In some implementations, determining the volatile content of the process stream based on the sample volatile content can include implementing a processing algorithm for processing raw data generated during the detecting of the vaporized volatiles in the gas phase in the detection zone 102. The processing algorithm can be based on a mass transfer model describing the removal of volatiles from a sample through gas stripping.

In some implementations, when the volatile content is a light hydrocarbons content, the light hydrocarbons content of the process stream can be determined according to a correlation between vaporized light hydrocarbons contents and non-vaporized light hydrocarbons contents. As used herein, the reference to a non-vaporized light hydrocarbons content refers to the content of light hydrocarbons that would be vaporized to a gas phase from a liquid phase using a stripping gas such as air, at conditions that would not vaporize heavier hydrocarbons such as bitumen or heavy oil therefrom. In other words, the measurement of non-vaporized light hydrocarbons refers to the light hydrocarbons that are in liquid phase in a sample of the process stream and that has not been subjected to stripping to vaporize the light hydrocarbons therefrom. Thus, measurements of non-vaporized light hydrocarbons refer to the light hydrocarbons that are in liquid phase in a sample of the process stream and that can be performed according to conventional techniques such as chromatography analysis.

In some implementations, the correlation thus establishes a relationship between values of light hydrocarbons contents that have been vaporized from respective test samples, which would correspond to vaporized light hydrocarbons contents, with values of light hydrocarbons contents in respective test samples that have been measured with conventional techniques, which would correspond to non-vaporized light hydrocarbons contents. For instance, tests can be performed on samples of the process stream that are subjected to stripping as described herein, and correlated with light hydrocarbons contents that are measured in process streams using conventional techniques. In some implementations, determining a correlation between the vaporized light hydrocarbons content of a sample and the non-vaporized light hydrocarbons content of the sample can include measuring the vaporized light hydrocarbons content of test samples of a test process stream using gas stripping as described herein to obtain a set of vaporized light hydrocarbons contents. Then, the non-vaporized light hydrocarbons content of the test samples of the test process stream can be measured with any appropriate technique to obtain a set of non-vaporized light hydrocarbons contents. The vaporized light hydrocarbons contents of the test samples can subsequently be correlated with the non-vaporized light hydrocarbons contents of the test samples to obtain the correlation.

Figure 7:
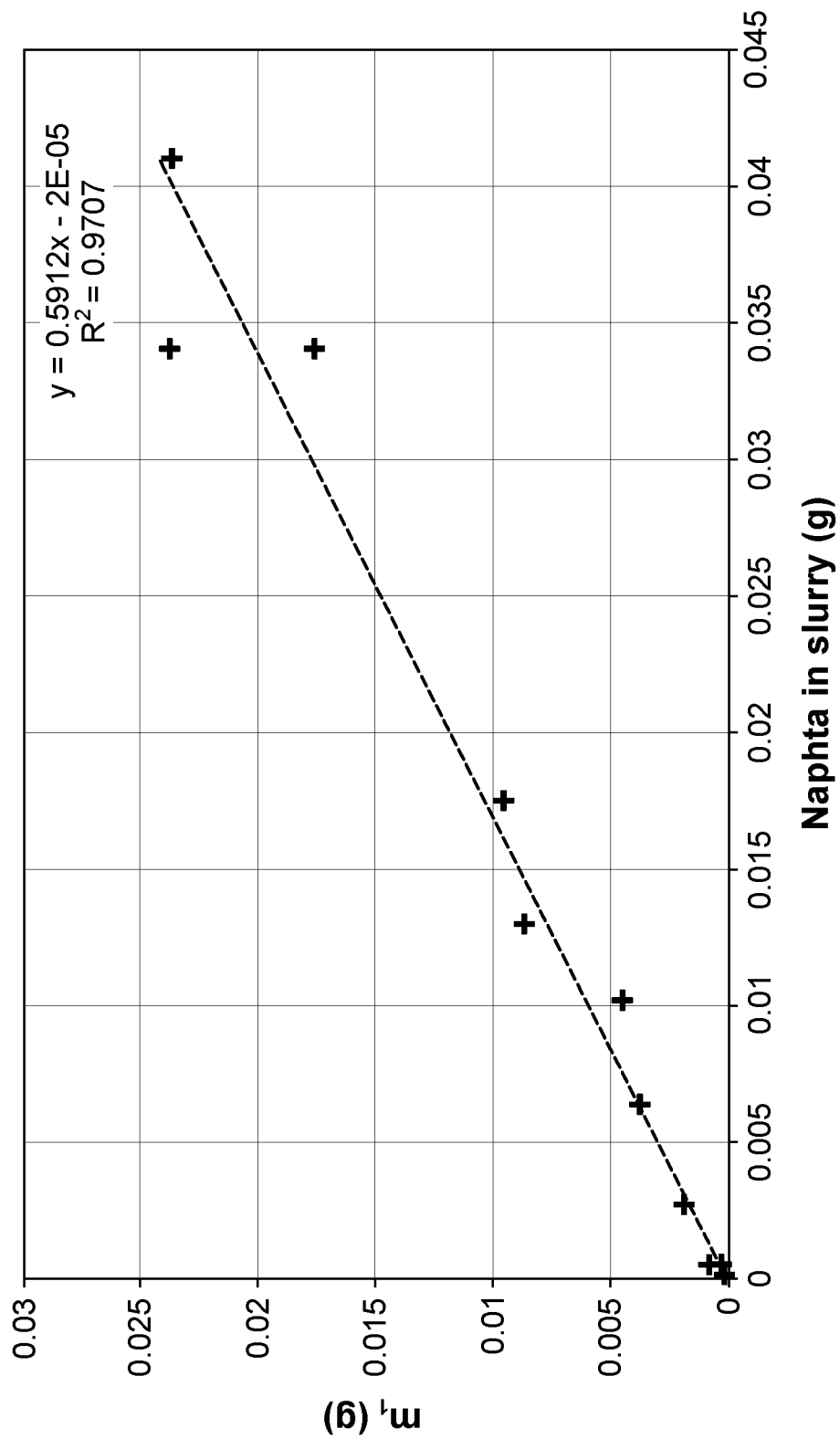
FIG. 7 is a graph of light hydrocarbons measurements in gas phase and in a slurry phase illustrating a correlating therebetween.

FIG. 7 illustrates an example of a correlation that can be obtained when measuring the vaporized light hydrocarbons content of different test samples of process streams using the volatile content measuring device 72 as described herein, i.e., light hydrocarbons content in gas phase, and associated non-vaporized light hydrocarbons content, i.e., light hydrocarbons content measurements in liquid phase, measured on the test samples of the process streams by conventional methods. In the example shown in FIG. 7, naphtha contents were measured on samples of froth treatment tailings.

Figure 5:
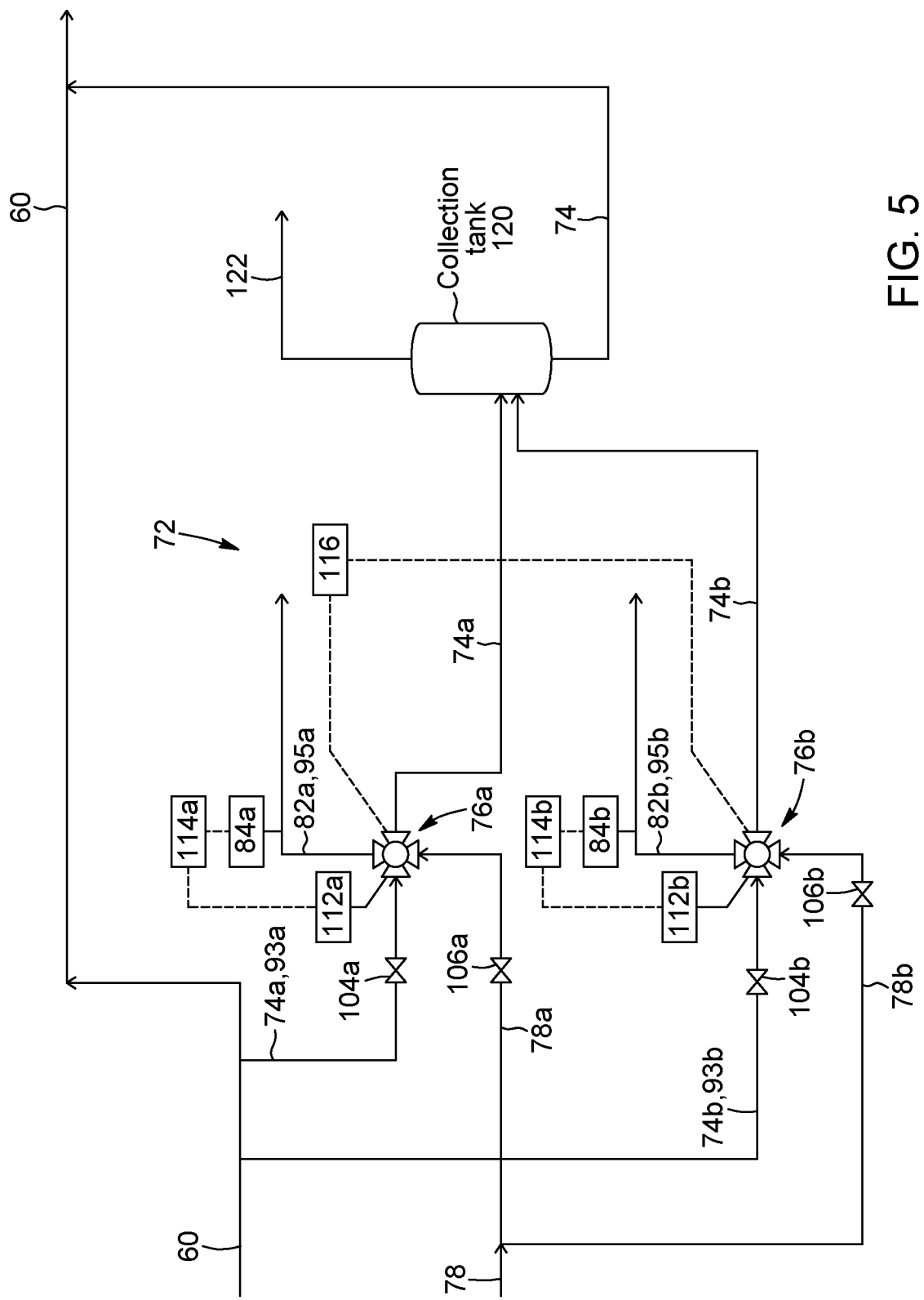
FIG. 5 is a process flow diagram illustrating an implementation of a volatile content measuring device that includes two four-way valves, the volatile content measuring device being provided in fluid communication with a stream of light hydrocarbons-depleted tailings from a light hydrocarbons removal unit.

Example Implementation of a Volatile Content Measuring Device and Associated Control Referring now to FIG. 5, an example implementation of a process for measuring a light hydrocarbons content using two volatile measuring devices 72 used in parallel is shown. Is it to be understood that although the example illustrated in FIG. 5 is to measure a light hydrocarbons content, the volatile measuring devices can alternatively be used to measure a $H_2S$ content, or a first volatile content measuring device can be used to measure a light hydrocarbons content and a second volatile content measuring device can be used to measure a $H_2S$ content, or both volatile content measuring devices can be configured to measure a light hydrocarbons content and a $H_2S$ content.

In the illustrated implementation, the light hydrocarbons-depleted tailings 60 is divided into two sub steams 74, each being in fluid communication with a corresponding four-way valve 76. Similarly, the stripping gas 78 is divided into two streams, each one being in fluid communication with a corresponding four-way valve 76. For ease of reference, the first and second sub streams 74 are represented with reference numbers 74a and 74b, respectively, the first and second streams of stripping gas 78 are represented with reference numbers 78a and 78b, respectively, and the two four-way valves 76 are represented with reference numbers 76a and 76b, respectively.

When two or more four-way valves 76 are implemented in parallel, for instance according to the scheme presented in FIG. 5, data representative of the light hydrocarbons content of the corresponding sub streams can be continuously collected to contribute to provide a "live" assessment of the light hydrocarbons content in the main line of the light hydrocarbons-depleted tailings 60. This can be achieved as when one of the volatile measuring device 72 is in a mode to collect data on the sample of the process stream to provide a concentration of the light hydrocarbons therein (i.e., in a stripping configuration), another volatile measuring device 72 can be in a receiving mode to receive a sample of the process stream (i.e., in a filling configuration), such that the alternance of these two modes provides a continuous monitoring of the light hydrocarbons content of the process stream.

In a first phase of the process, the light hydrocarbons-depleted tailings 60 can be continuously fed through the four-way valves 76a, 76b, via the respective sub streams 74a, 74b, such that the four-way valves 76a, 76b can be considered as being in the first configuration as described above. The flow through the four-way valves 76a, 76b can be driven by the pressure in the process lines, or alternatively, a pump 88 can be provided as shown in FIGS. 2A and 2B to supply the sub streams 74a, 74b to the four-way valves 76a, 76b.

In the implementation shown, when in the first configuration, the sub streams 74a, 74b are routed to a collection tank 120, at a rate that can be dependent on the pressure in the pipeline transporting the light hydrocarbons-depleted tailings 60 and on the opening of the valves 104a, 104b. As mentioned above, when the four-way valves 76a, 76b are in the second configuration, the valves 104a, 104b can be closed to prevent the sub streams 74a, 74b to be supplied to the respective four-way valves 76a, 76b. Alternatively and as shown in FIGS. 2A and 2B, the sub streams 74a, 74b can also be routed directly back to the light hydrocarbons-depleted tailings 60.

The collection tank 120 can be in equilibrium with the atmosphere, and can be configured to vent gases 122 by returning them to the atmosphere. A pump (not shown) can be provided downstream of the collection tank 120 to return the sub stream 74 to the main line of the light hydrocarbons-depleted tailings 60. The pump can be operated in an on/off mode. For instance, the pump can be turned on when the content level of the collection tank 120 reaches a given high level threshold, and turn off when the content level of the collection tank 120 is below a given low level threshold. In addition, although not shown in FIG. 5, the gas phase streams 82a, 82b can also be routed to the collection tank 120 if desired.

In a second phase of the process, the second four-way valve 76b can be switched to the second configuration. In the second configuration, the valve 104b can be closed to prevent the sub stream 74b to reach the four-way valve 76b. The valve 106b is opened to enable the stripping gas 78b to be supplied to the four-way valve 76b. Thus, in the second phase of the process, the first four-way valve 76a can remain in the first configuration where the valve 104a is opened and the sub stream 74a passes through the four-way valve 76a, and the second four-way valve 76b can be switched to the second confirmation where the valve 104b is closed and the sub stream 74b is prevented to pass through the four-way valve 76b. Still in the second phase of the process, the valve 106b is opened to enable the stripping gas 78b to be supplied to the four-way valve 76b. In some implementations, a configuration indicator 112a, 112b can be provided to monitor the state of a respective four-way valves 76a, 76b.

The stripping gas 78b is supplied to the four-way valve 76b to strip the sample of the sub stream 74b that is retained in the sample chamber 100 of the four-way valve 76b. The light hydrocarbons content in the gas phase stream 82b can be monitored over time using the detection device 84, until a pre-determined timepoint determined by a data processing algorithm, which can be programmed in a controller 114b.

In some implementations, the sampling time to enable detection of the light hydrocarbons content in the gas phase 82b can range from about 1 minute to about 15 minutes, or from about 5 minutes to 10 minutes. A shorter sampling time for the detection device 84b to generate data representative of the light hydrocarbons present in the sample being analyzed can be beneficial to provide an accurate "live" estimate of the concentration of the light hydrocarbons in the sub stream 74b, and thus in the light hydrocarbons-depleted tailings 60. Different strategies can also be implemented to reduce the sampling time and thus reducing the time for collecting representative data. For instance, the amount of stripping gas bubbles introduced into the sample of sub stream 74 can be increased. The amount of stripping gas bubbles introduced into the sample of sub stream 74 can be increased for example by increasing the flow rate of the stripping gas 78, and by modifying the configuration of the sparger 124. Modifying the configuration of the sparger 124 can include for instance providing a higher number of openings in the sparger, modifying the spatial distribution of the openings, etc. Providing heat to the sub stream 74 or the sample being analyzed can also contribute to facilitating the vaporization of the light hydrocarbons to the gas phase 82. For example, as mentioned above, the sub stream 74 or the sample being analyzed can be heated to a temperature ranging from about 25° C. to about 70° C. to facilitate stripping and vaporization of the light hydrocarbons to the gas phase 82.

Using the data processing algorithm, the controller 114b can process the data from the detection device 84b to provide an estimate of the total light hydrocarbons in the sample. Since the starting volume of the sample is known, the concentration in units of mass of light hydrocarbons per unit of volume can be calculated and displayed. Alternatively, a mass concentration can be determined if the density of the sample is known.

In some implementations, the gas stripping can be performed to enable discrimination of the light hydrocarbons that are present in the sample of the process stream following their addition thereto, i.e., present as an additive to the process stream, and the species that are native to bitumen, and more particularly those of the front-end of the bitumen phase.

The controller 114b can also be operatively connected to a valve controller 116. In a third phase of the process, once the content of the light hydrocarbons in the sample has been obtained, a signal can be sent to the valve controller 116 by the controller 114b in order to switch the second four-way valve 76b from the second configuration back to the first configuration. A signal can also be sent to the valve controller 116 by the controller 114a to switch the first four-way valve 76a from the first configuration to the second configuration. When the first four-way valve 76a is switched to the second configuration, the valve 104a can be closed to prevent flow of the sub stream 74a to the four-way valve 76a, and the valve 106a can be opened to enable the stripping gas 78a to be supplied to the first four-way valve 76a and through the sample to strip the light hydrocarbons therefrom.

Once the first four-way valve 76a is switched to the second configuration, the steps described above regarding the operation of the second four-way valve 76b can be performed similarly to obtain a value of the light hydrocarbons content in the sub stream 74a using detection device 84a, while the second four-way valve 76b enables passage of the sub stream 74b therethrough so as to fill the sample chamber with another sample that will be subsequently analyzed by the detection device 84b.

In some implementations, a purge step may be implemented when a four-way valve 76 is switched from the second configuration to the first configuration to ensure that residual light hydrocarbons that could remain in the detection zone 102 are removed. The purge step can be performed for instance by flowing a liquid such as water, or a gas such as air into the detection zone 102, to avoid carry-over between samples being analyzed. The stripping gas pipeline section 95 carrying the gas phase 82 downstream of the four-way valve 76 can thus be equipped with additional lines and valves for flushing and purging the detection zone 102.

In the scheme detailed above with regard to FIG. 5, the operation of the two four-way valves 76a, 76b is described as being successive, i.e., once the second phase is completed and data has been collected by the detection device 84b, the third phase is initiated and data can be collected by the detection device 84a. In other implementations, the two four-way valves 76a, 76b can be operated such that the second and third phases overlap each other. When the second and third phases overlap each other, or are offset in time, additional data can be collected in a shorter time frame, which can be beneficial in the context of live monitoring of process streams.

In addition, more than two four-way valves can be implemented, and operated either successively or in an overlap, or according to a combination of both.

Once data regarding the light hydrocarbons content of the light hydrocarbons-depleted tailings 60 has been collected, the data can be assessed with regard to a given specification that is to be achieved. For instance, if it has been determined that the specification, or the predetermined threshold, for the light hydrocarbons content of the light hydrocarbons-depleted tailings 60 is to be below 200 ppm, for example, then it can be determined whether operating parameters of the light hydrocarbons removal unit 56 should be adjusted to correct a potential deviation from the specification. The data can also be assessed to determine whether the given specification, or predetermined threshold, is met for the light hydrocarbons-depleted tailings 60 to be discharged to a permanent aquatic storage structure or any other type of deposition site configured for receiving tailings material for dewatering.

The implementation shown in FIG. 5 is presented in the context of the treatment of MFT-affected tailings 52 in a light hydrocarbons removal unit 56 to remove light hydrocarbons therefrom. However, the volatile content measuring device 72 can be implemented in accordance with the scheme illustrated in FIG. 3 or in FIG. 5 at any of the locations shown in FIG. 1, and can be implemented to measure other types of volatiles than light hydrocarbons, such as H$_2$S. In addition, the volatile content measuring device 72 can be implemented for determining a light hydrocarbons content and/or a H$_2$S content in any other process stream that contains light hydrocarbons or H$_2$S, either in the oil sands industry or in other industries where live monitoring of light hydrocarbons content, such as naphtha, or H$_2$S can be beneficial.

In addition, a four-way valve has been described as an example of a device that can be used to collect a sample of a process stream to be analyzed within a sample chamber having a measurable volume, such that the amount of volatiles stripped and vaporized to the gas phase can be converted to an amount of volatiles in liquid phase, i.e., in the process stream. The four-way valve also offers the opportunity of switching to a configuration that enables introduction of the stripping gas into the sample. It is to be understood that any other physical structure, or device, that enables receiving a measurable volume of a sample to be analyzed, stripping of the sample to strip volatiles therefrom to a gas phase and subsequent measuring of the volatile content in the gas phase can also be suitable. Ideally, such device can be installed on-line, and is configured to assess a sample having a volume in the range of 50 mL to 1 L, to facilitate stripping of the volatiles therefrom, which in turn can contribute to provide "live" volatile content on the process stream being monitored. As mentioned above, the device can thus be considered a scaled down, or miniaturized, stripping process that is installed in parallel to the pipeline transporting the process stream for which live monitoring of volatiles, such as diluent, is desired.

Although not shown in FIG. 5, it is to be understood that the volatile content measuring device 72 can include the heater 103, the expander 107 and/or the filter 109 described above, as desired.

It is to be understood that although the expression "live monitoring" is used herein to characterize the monitoring of the volatile content in the process stream analyzed, there can be a delay between the timepoint when the sample is collected in the sample chamber and the data provided by the detection device. This delay is associated with the time used to strip the sample, i.e., to vaporize the volatiles to a gas phase. However, as mentioned above, the time to strip the sample can range from about 1 minute to about 15 minutes, depending for instance of the volume of the sample collected, amongst other variables, and this time delay is considered to be sufficiently short to be considered within the timescale of live monitoring. In addition, when a plurality of volatile content measuring devices 72 are implemented in parallel, such as illustrated in FIG. 5, data regarding the volatile content of the process stream can continuously be collected, thereby contributing the live monitoring of the process stream.

In addition, the detection device 84 can be any type of detection device that enables measurement of volatiles in gas phase.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A method for measuring a volatile content of a process stream comprising volatiles, the method comprising:
   receiving a sample of the process stream into a sample chamber having a chamber volume;
   introducing a stripping gas into the sample of the process stream to strip the volatiles therefrom and produce a gas phase comprising vaporized volatiles;
   detecting the vaporized volatiles in the gas phase to obtain a sample volatile content; and
   determining the volatile content of the process stream based on the sample volatile content.

2. The method of claim 1, wherein introducing the stripping gas into the sample of the process stream comprises sparging the stripping gas into the sample.

3. The method of claim 1, wherein receiving the sample of the process stream into the sample chamber comprises flowing the process stream through the sample chamber until a predetermined timepoint is reached, and retaining the sample of the process stream into the sample chamber.

4. The method of claim 1, wherein the volatiles comprise light hydrocarbons.

5. The method of claim 4, wherein the light hydrocarbons comprise naphtha, toluene, light aromatic compounds, C3 to C7 aliphatic compounds, natural gas condensate, or a combination thereof.

6. The method of claim 1, wherein detecting the vaporized volatiles in the gas phase to obtain the sample volatile content comprises measuring the sample volatile content via photoionization.

7. The method of claim 1, wherein the volatiles comprise $H_2S$, and detecting the vaporized volatiles in the gas phase to obtain the sample volatile content comprises measuring the sample volatile content via a $H_2S$ sensor.

8. The method of claim 1, further comprising heating the sample of the process stream prior to detecting the vaporized volatiles in the gas phase, to accelerate the stripping of the volatiles therefrom.

9. The method of claim 1, wherein the process stream comprises a wastewater stream.

10. The method of claim 9, wherein the wastewater stream comprises refinery wastewater.

11. The method of claim 1, wherein the process stream comprises a process stream derived from refinery operations.

12. A process for producing a hydrocarbon product, comprising:
   treating a feedstock to produce the hydrocarbon product and an associated process stream;
   measuring a volatile content of the associated process stream, comprising:
   supplying a sample of the associated process stream to a sample chamber having a chamber volume, the sample chamber being configurable to be in fluid communication with the associated process stream;
   introducing a stripping gas from a stripping gas supply into the sample of the associated process stream to strip the volatiles therefrom and produce a gas phase comprising vaporized volatiles, the gas phase being receivable in a detection zone in fluid communication with the sample chamber, the detection zone being further configurable to be in fluid communication with the stripping gas supply;
   detecting the vaporized volatiles in the gas phase received in the detection zone to obtain a sample volatile content; and
   determining the volatile content of the associated process stream based on the sample volatile content.

13. The process of claim 12, further comprising measuring the volatile content of the hydrocarbon product.

14. The process of claim 13, wherein treating the feedstock comprises refining and the hydrocarbon product comprises a refinery-derived product.

15. The process of claim 13, further comprising adjusting the treating of the feedstock based on the volatile content of the hydrocarbon product or of the associated process stream.

16. The process of claim 12, wherein the associated process stream comprises a wastewater stream.

17. The process of claim 16, wherein the wastewater stream comprises refinery wastewater and the hydrocarbon product comprises a refinery-derived product.

18. The process of claim 12, wherein the associated process stream comprises froth treatment tailings, the hydrocarbon product comprises diluted bitumen, and the feedstock comprises oil sands material.

19. The process of claim 13, wherein the volatiles comprise light hydrocarbons.

20. A device for measuring a volatile content of a process stream comprising volatiles, the device comprising:
   a sample chamber having a chamber volume, the sample chamber being configured for receiving a sample of the process stream;
   a stripping gas supply for introducing a stripping gas into the sample of the process stream to strip the volatiles therefrom and produce a gas phase comprising vaporized volatiles, the sample chamber being configured to be alternately in fluid communication with the process stream or with the stripping gas supply;
   a detection zone in fluid communication with the sample chamber to receive the gas phase comprising the vaporized volatiles; and
   a detection device extending within the detection zone to measure a sample volatile content of the sample that is convertible to the volatile content of the process stream.

21. The device of claim 20, wherein the device is installable on-line to a pipeline through which the process stream flows, to provide live monitoring of the volatile content of the process stream.

22. The device of claim 20, further comprising a sparger downstream of the stripping gas supply to introduce bubbles of the stripping gas into the sample.

23. The device of claim 20, further comprising a heater operatively connected to the sample chamber and configured to heat the sample to accelerate the stripping of the volatiles therefrom prior to detecting the vaporized volatiles in the gas phase.

24. The device of claim 20, wherein the detection device comprises a photoionization system configured to measure the volatile content when the volatiles comprise light hydrocarbons.

* * * * *